United States Patent [19]
Oriol et al.

[11] Patent Number: 5,957,855
[45] Date of Patent: *Sep. 28, 1999

[54] FETAL DATA PROCESSING SYSTEM AND METHOD EMPLOYING A TIME-FREQUENCY REPRESENTATION OF FETAL HEART RATE

[75] Inventors: Nancy E. Oriol, Cambridge; Frederick M. Bennett, Holden, both of Mass.

[73] Assignee: Beth Israel Deaconess Medical Center, Boston, Mass.

[ * ] Notice: This patent is subject to a terminal disclaimer.

[21] Appl. No.: 08/809,401

[22] PCT Filed: Sep. 21, 1995

[86] PCT No.: PCT/US95/12014

§ 371 Date: May 29, 1997

§ 102(e) Date: May 29, 1997

[87] PCT Pub. No.: WO96/08996

PCT Pub. Date: Mar. 28, 1996

Related U.S. Application Data

[63] Continuation-in-part of application No. 08/309,856, Sep. 21, 1994, Pat. No. 5,596,993.

[51] Int. Cl.⁶ .................................................. A61B 5/0444
[52] U.S. Cl. .................. 600/511; 600/523; 600/483; 600/408
[58] Field of Search ...................... 600/301, 408, 600/437, 453, 481, 483, 500, 508, 511, 528, 515, 523, 586, 591; 607/902

[56] References Cited

U.S. PATENT DOCUMENTS

| | | | |
|---|---|---|---|
| 3,599,628 | 8/1971 | Abbenante et al. | 128/678 |
| 4,781,200 | 11/1988 | Baker | 600/483 |
| 4,890,624 | 1/1990 | Ganguly et al. | 128/661.07 |
| 5,042,499 | 8/1991 | Frank et al. | 128/698 |
| 5,265,613 | 11/1993 | Feldman et al. | 120/661.07 |
| 5,442,940 | 8/1995 | Secker et al. | 600/453 |
| 5,596,993 | 1/1997 | Oriol et al. | 600/511 |
| 5,623,939 | 4/1997 | Garfield | 600/546 |

FOREIGN PATENT DOCUMENTS

93/08534  4/1993  WIPO .

OTHER PUBLICATIONS

Brochure and diskette regarding Ansar Medic Monitor ANS–R1000 Real Time Non–Invasive Power Spectrum Heart Rate Analysis.

Brochure entitled "System 8000 Sonicaid Antepartum Fetal Heart Rate Analysis," Oxford Instruments Medical Systems Division.

Hlawatsch, F., et al., "Linear and Quadratic Time–Frequency Signal Representations," *IEEE Signal Processing Magazine*, pp. 21–67, (Apr. 1992).

Mantel, R., et al., "Automated analysis of near–term antepartum fetal heart rate in relation to fetal behavioral states: The Sonicaid System 8000," *Am. J. Obstet. Gynecol.*, 165(1):57–62, (Jul. 1991).

Novak, P., et al., "Time/frequency mapping of the heart rate, blood pressure and respiratory signals," *Medical & Biological Engineering & Computing*, 31:103–110, (Mar. 1993).

(List continued on next page.)

*Primary Examiner*—William E. Kamm
*Assistant Examiner*—Kennedy J. Schaetzle
*Attorney, Agent, or Firm*—Hamilton, Brook, Smith & Reynolds, PC

[57]  ABSTRACT

A fetal data processing system and method, and a fetal monitor and method for monitoring the condition of a fetus are disclosed. A fetal heart rate time series is received and sampled. A non-linear time-frequency transformation is performed to generate a time-frequency representation of the fetal heart rate time series for heart rate time series data spanning a time period which is preferably less than ten seconds. Analysis of fetal heart rate and fetal heart rate variability and other available data is performed to evaluate fetal well-being. Because of the high time resolution of the transformation, short-term transient variations in the heart rate and heart rate variability are considered in the analysis.

36 Claims, 14 Drawing Sheets

OTHER PUBLICATIONS

Hyndman, B. W., et al., "Spectral analysis of heart rate variability revisited. Comparison of the methods," Preprint, *Computers in Cardiology,* London, 1993, pp. 1–4.

Abboud, S., et al., "Power spectrum analysis of fetal heart rate variability using the abdominal maternal electrocardiogram," *J. Biomed. Eng.,* 12:161–162, (Mar. 1990).

Chess, et al., "Spectral analysis as a diagnostic aid in the management of high–risk pregnancy," *Am. J. Obstet. Gynecol.,* pp. 471–474, (Feb. 1976).

Karin, J., et al., "An Estimate of Fetal Automatic State by Spectral Analysis of Fetal Heart Rate Fluctuations," *Pediatric Research,* 34(2):134–138, (1993).

Dawes, G. S., et al., "Computerized analysis of episodic changes in fetal heart rate variation in early labor," *Am. J. Obstet. Gynecol.,* 165(3):618–624, (Sep. 1991).

Beksac, M. S., et al., "The validation of a computerized system for the interpretation of the antepartum fetal heart rate tracings (version 89/2.34)," *European Journal of Obstetrics & Gynecology and Reproductive Biology,* 42:9–14 (1991).

Mantel, R., et al., "Computer Analysis of Antepartum Fetal Heart Rate: 1. Baseline Determination," *Int. J. Biomed. Comput.,* 25:261–272, (1990).

Mantel, R., et al., "Computer Analysis of Antepartum Fetal Heart Rate: 2. Detection of Accelerations and Decelerations," *Int. J. Biomed. Comput.,* 25:273–286, (1990).

Pello, L. C., et al., "Computerized Fetal Heart Rate Analysis in Labor," *Obstetrics & Gynecology,* 78(4):602–610, (Oct. 1991).

Lilja, H., et al., "Fetal ECG during labour: a presentation of a microprocessor system," *J. Biomed. Eng.,* 10:348–350, (Jul. 1988).

van Ravenswaaij–Arts, C.M.A., et al., "Heart Rate Variability," *Annals of Internal Medicine,* 118(6):436–447, (Mar. 1993).

Stein, P. K., et al., "Heart rate variability: A measure of cardiac autonomic tone," *American Heart Journal,* 127(5):1376–1381, (1994).

Rouwendaal, F.T.N., et al., "The HRV–Explorer: An Object–Oriented Workstation for the Analysis of Large RR–interval Databases," Preprint, *Computers in Cardiology,* London, 1993, pp. 1–4.

Thaler, I., et al., "Interpretation of the fetal ECG during labor: the effect of uterine contractions," *J. Perinat. Med.,* 16:373–379, (1988).

Field, D. R., et al., "Fetal heart rate variability and cerebral oxygen consumption in fetal sheep during asphyxia," *European Journal of Obstetrics & Gynecology and Reproductive Biology,* 42:145–153, (1991).

Arduini, D., et al., "Quantitative Analysis of Fetal Rate: Its Application in Antepartum Clinical Monitoring and Behavioral Pattern Recognition," *Int. J. Biomed. Comput.,* 25:247–252, (1990).

Novak, V., et al., "Influence of respiration on heart rate and blood pressure fluctuations," *American Physiological Society,* pp. 617–626, (1993).

Pincus, S. M., et al., "Approximate Entropy: A Regularity Measure for Fetal Heart Rate Analysis," *Obstetrics & Gynecology,* 79(2):249–255, (Feb. 1992).

Darvish, N., et al., "Time–Frequency and Time–Scale Methods in the Detection and Classification of Non–Stationarities in Human Physiological Data," IEEE, pp. 1085–1089, (1995).

Power Spectral Heart Rate Analysis, ANSARinc and Medic Monitor ANS–R1000, consisting of 4 sheets.

Novak et al., "Time/frequency mapping of the heart rate, blood pressure and respiratory signals," Medical& Biological Eng. & Computing, pp. 103–110, Mar. 1993.

Ifeachor et al., "Techniques and Applications of Neural Networks," Chapter 6, pp. 93–107, 1992.

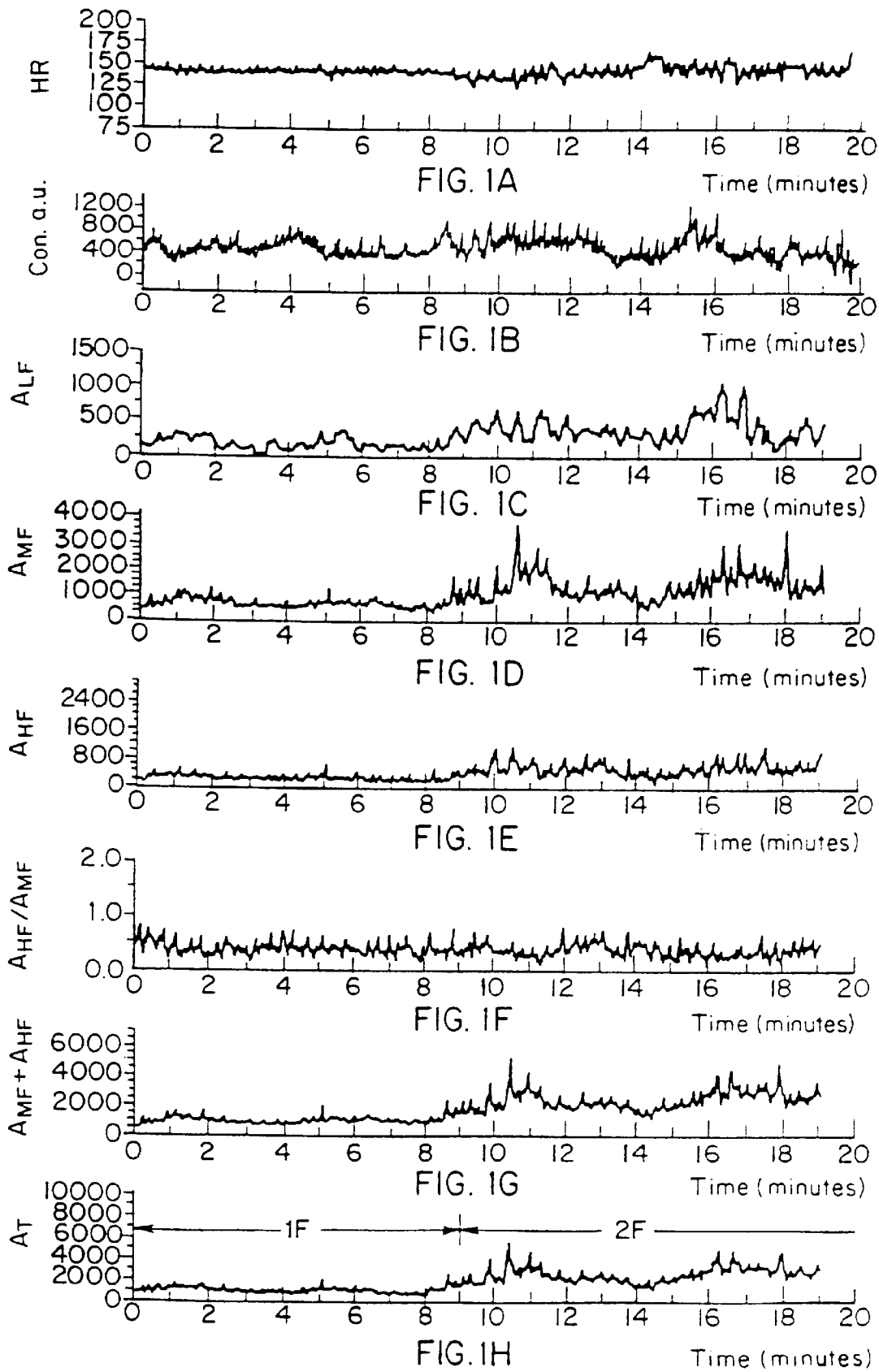

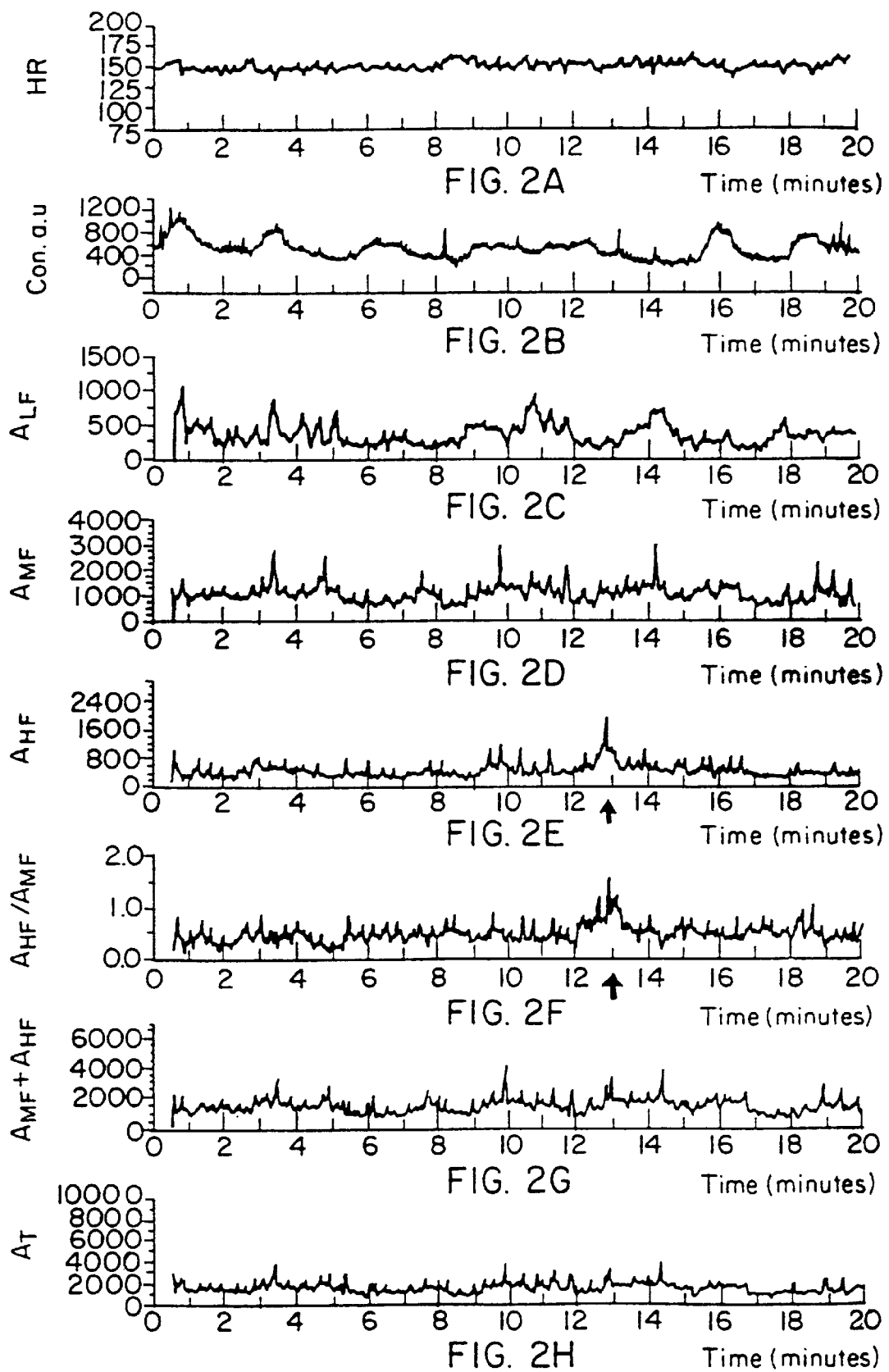

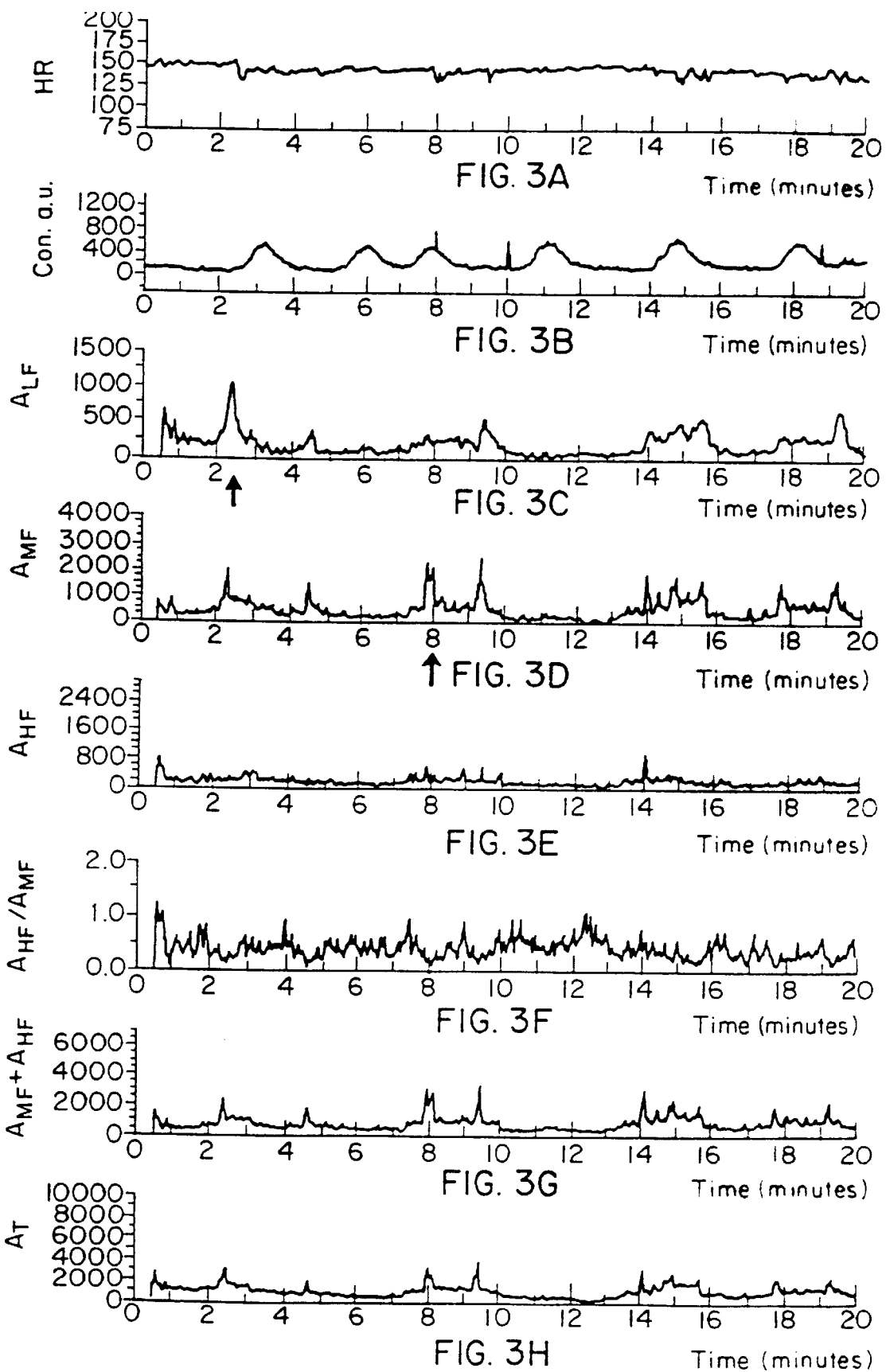

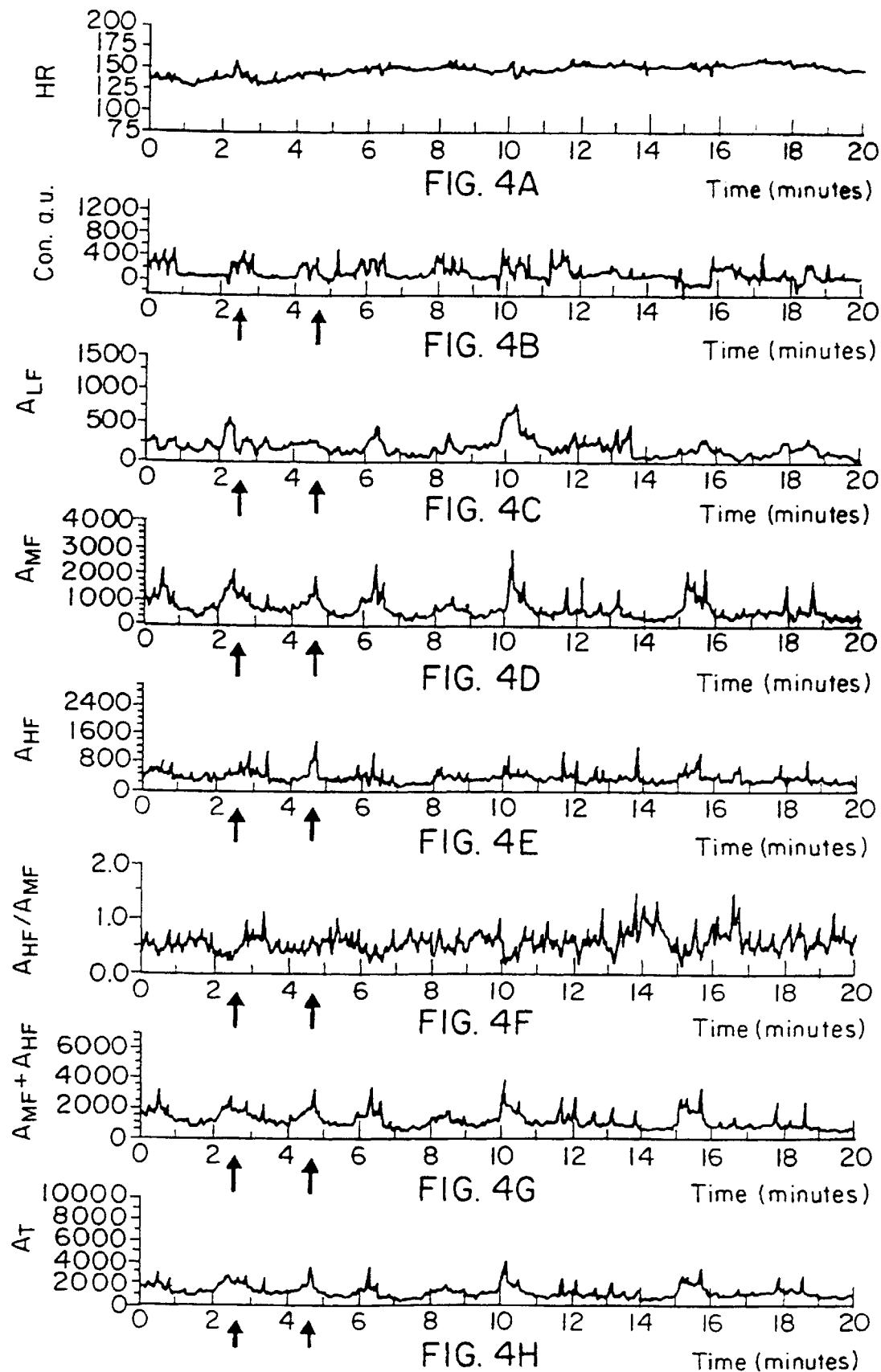

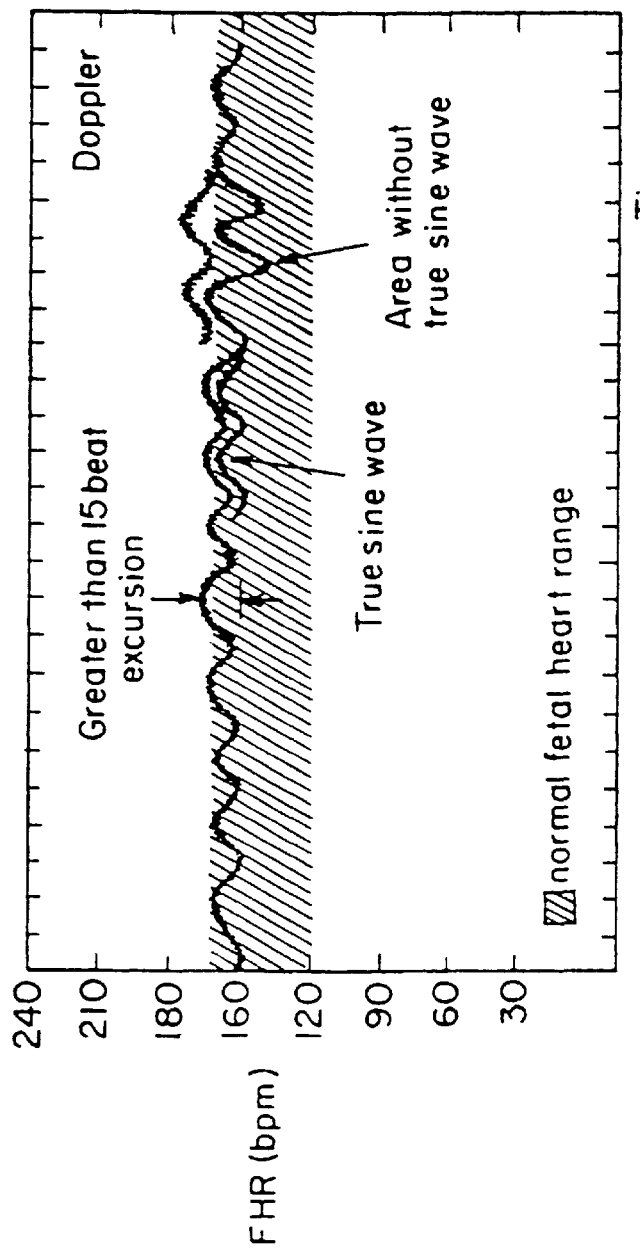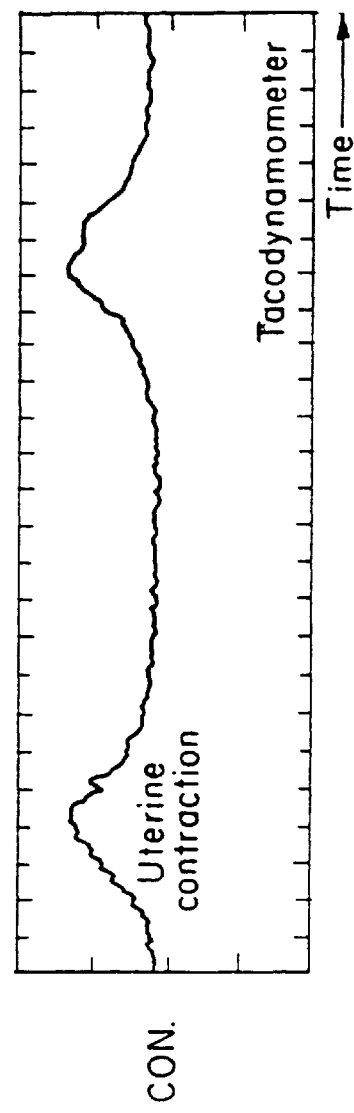

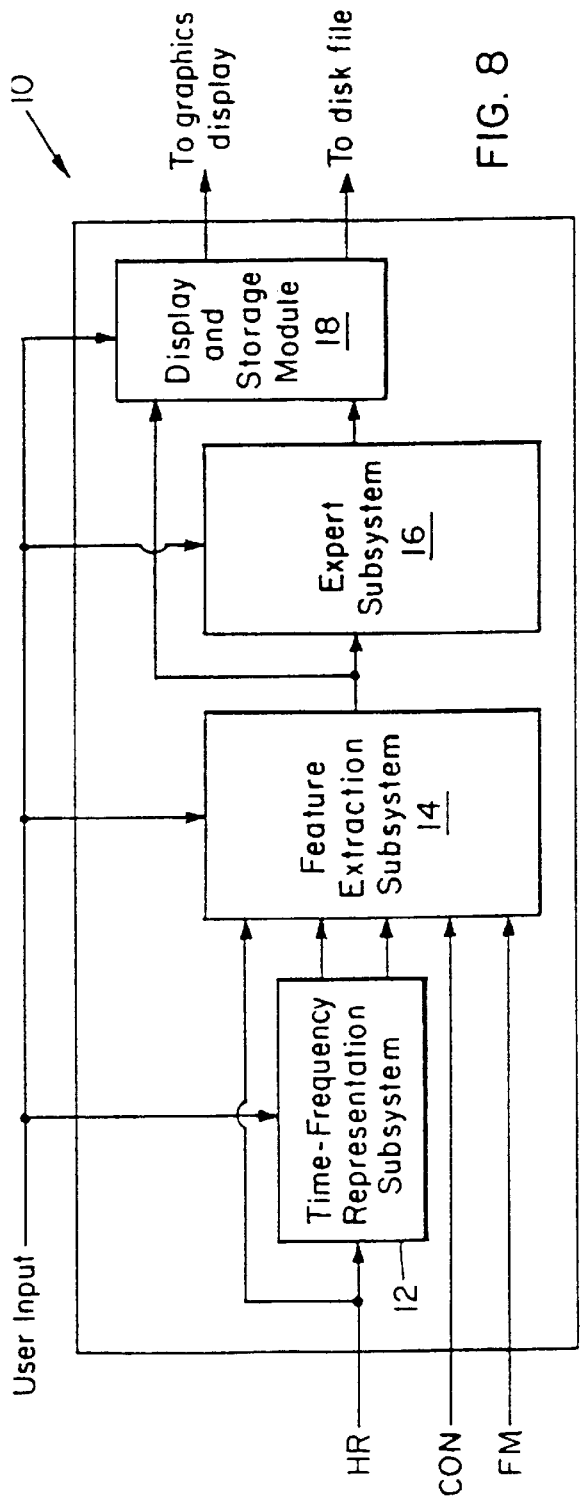
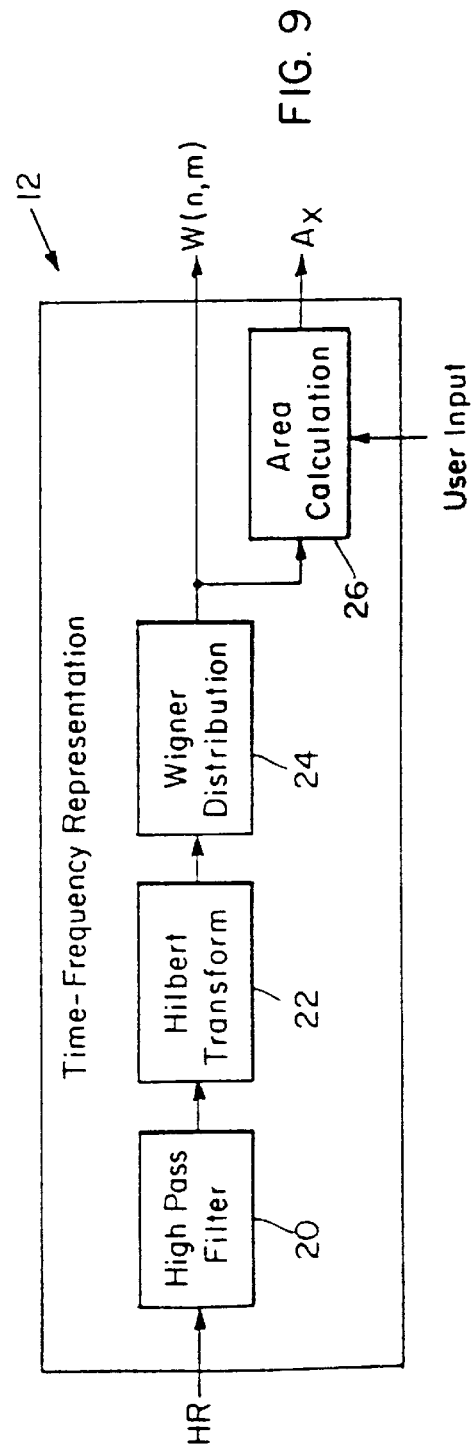
FIG. 8
FIG. 9

FETAL DATA PROCESSING SYSTEM AND METHOD EMPLOYING A TIME-FREQUENCY REPRESENTATION OF FETAL HEART RATE

RELATED APPLICATIONS

This is a U.S. National Phase Application of International Application No. PCT/US95/12014 filed on Sep. 21, 1995 which is a continuation-in-part application of U.S. Ser. No. 08/309,856 filed on Sep. 21, 1994, now U.S. Pat. No. 5,596,993, the entire contents of the above related applications being incorporated herein by reference.

BACKGROUND OF THE INVENTION

Fetal monitors of various types are widely used in the obstetrics field. Most of the devices provide to the clinician an indication of fetal heart rate (HR) as one item of data used by the clinician to evaluate overall fetal well-being. Other more sophisticated devices perform frequency analysis on heart rate time data to produce indications of heart rate variability (HRV), another very important item of data used to monitor fetal condition.

Typically, these frequency analysis devices collect fetal heart rate time data over relatively long periods of time. At the end of each period, a linear time-frequency representation, such as a short-term Fourier transform or a fast Fourier transform, is computed on the time data to obtain a frequency distribution for the data. In one such prior system, each time data window is 30–60 seconds in duration.

A significant drawback to these devices is that, because of the long time data window duration, or, equivalently, the low time resolution of the device, short term or transient variations in heart rate and/or heart rate variability cannot be detected. These transient changes can be indicators of significant fetal characteristics such as fetal breathing and should be considered in evaluating overall fetal well-being. Because these prior systems have long time windows, transient changes are not detected, and, therefore the often critically important fetal characteristics associated with the transient changes are not taken into consideration in the overall fetal evaluation.

SUMMARY OF THE INVENTION

The present invention is directed to a fetal data processing system and method and a fetal monitor and method for monitoring fetal condition which overcomes the drawbacks of prior art monitors. Specifically, the invention analyzes fetal heart rate data in both time and frequency domains with sufficient time resolution to detect transient changes in fetal heart rate and fetal heart rate variability while also detecting other important heart rate and heart rate variability characteristics. The invention also has sufficient frequency resolution to provide a substantial improvement in accuracy of frequency analysis and in diagnostic capabilities over prior systems. This is particularly true during the human birthing process and/or when the mother or fetus are at risk due to medication, disease, injury, or other reason.

The system or monitor of the invention receives fetal heart rate time data and samples the data at preferably periodic intervals. The invention transforms the time data into the frequency domain by computing a time-frequency representation (TFR), in one embodiment, a non-linear TFR, for the time data. In one embodiment, a non-linear TFR is computed for time data covering a time interval of no more than ten seconds; the time interval is preferably in the range between 0.1 and 1.0 second. The system then analyzes the non-linear TFR to indicate a condition of the fetus.

In one embodiment, the time data is sampled at 0.25 second intervals. For each sample in this embodiment, the invention computes a non-linear time-frequency representation (TFR) of the data. It then analyzes the non-linear TFR to indicate the condition of the fetus and to indicate fetal well-being. In other embodiments, the data is sampled at the same 0.25 second interval, but the TFR may not be calculated on every data sample. Instead, it may be calculated at greater intervals. Preferably, the interval between recalculation of the TFR will not exceed ten seconds.

As noted above, the sampling interval is preferably 0.25 second or, equivalently, the sampling frequency is preferably 4 Hz. Other sampling frequencies can be used. However, the frequency will preferably never be below 2 Hz to meet the Nyquist criterion for certain signal frequencies in heart rate data near 1 Hz, as will be described below in detail. Lower sampling frequencies can be used if anti-aliasing filters are used.

In the system of the invention, the fetal heart rate time series is obtained from either a separate internal or external fetal heart monitor. The time series is first high-pass filtered to remove the DC and very low frequency components. Next, the signal is made analytic by a Hilbert Transform, and the non-linear time-frequency representation (TFR) is then obtained for the signal. In one preferred embodiment, the non-linear TFR is computed by a quadratic transformation process such as a smoothed Wigner distribution.

The TFR is essentially an amplitude-versus-frequency plot of the frequency content of the heart rate time series which is updated over time. There are a number of methods used to calculate TFRs. These include linear techniques such as the short-term Fourier transform, the wavelet transform and non-linear transformations belonging to the Cohen class of TFRs. The non-linear transformation results in substantial improvement in both temporal and frequency resolutions compared to the short-term Fourier transform. In the preferred embodiment, the smoothed Wigner transform is used, although other techniques from Cohen's class of TFRs, such as the Choi-Williams or Cone Kernel distributions could also be used. The wavelet transform, although a linear technique, has better time resolution, particularly at higher frequencies, than the short-term Fourier transform. The wavelet transform is an alternative method of calculating the TFR. Improved resolution in both the time and frequency domains allows for changes in the frequency content of the heart rate time signal to be quantified and located to a specific period of time. Thus, the system and monitor of the invention provide highly desirable frequency and temporal resolution to allow more accurate evaluation of overall fetal well-being.

In a preferred embodiment, for each new sample of heart rate, the non-linear TFR is calculated. Then, the area under the amplitude-frequency plot is calculated over specified frequency bands. These areas are then presented for display to the clinician and are also used by the monitor to assess fetal condition. As an example of the multiple frequency bands, sample areas are defined as follows:

$A_{HF}$: High frequency (HF) 0.50–1.1 Hz
$A_{MF}$: Mid frequency (MF) 0.15–0.50 Hz
$A_{LF}$: Low frequency (LF) 0.02–0.50 Hz The MF and HF bands are modulated solely by the parasympathetic nervous system since sympathetic modulation of heart rate is minimal above 0.15 Hz. The LF band should reflect both sympathetic and parasympathetic modulation of heart rate variability.

It will be understood that the frequency bands listed above, as well as the total frequency range, are used for illustration purposes only and not as limitations. Other frequency bands and ranges can be used. The definition of the frequency bands are based on current understanding of the physiology. These are envisioned as the default definitions. The user is able to enter new values for the frequencies defining the bands or even change the number of bands analyzed. In addition, the user has the capability of defining ratios and/or sums of pairs of areas.

In addition to monitoring the heart rate time series and heart rate variability, the invention can also monitor optional input signals. These include a uterine contraction signal and a fetal movement signal. By analyzing various combinations of the available input data, the invention can indicate several fetal characteristics. These include changes in fetal state, fetal breathing movements, fetal body movements, fetal heart rate accelerations and decelerations, fetal heart rate variability and transient changes in fetal heart rate and fetal heart rate variability.

The system of the invention includes numerous subsystems for processing and analyzing input data and assessing fetal condition. A time-frequency representation (TFR) subsystem performs the transformation of the heart rate time data into the frequency domain. It receives the heart rate time series data, high-pass filters the data, and performs the Hilbert Transform to make the heart rate signal analytic. Then, it calculates the non-linear TFR on the analytic heart rate signal, preferably by a smoothed Wigner distribution. As noted above, other specific implementations use other known non-linear transformations such as the Choi-Williams distribution. An area calculation module of the TFR subsystem computes the areas under the TFR.

A feature extraction subsystem receives as inputs the heart rate time series, the TFR, the area calculations, the uterine contraction signal and the fetal movement signal and analyzes the data to compile the data into a feature vector. The feature vector is a collection of data which includes values for all of the variables used to perform the fetal assessment process. These variables are periodically updated as the time series is sampled. That is, in one embodiment, a new feature vector is generated for every sample of the heart rate time series.

The feature vector and various user inputs are received by an expert subsystem of the invention. The principal function of the expert subsystem is to classify data contained in the feature vector and the user inputs to make an assessment of fetal condition and well-being. It includes multiple first-stage classifiers which receive the feature vector and make preliminary assessments as to fetal state, heart rate deceleration and acceleration patterns and uterine contraction pattern. In one embodiment, the initial or first-stage classifiers are rule-based. In other embodiments, one or more of them are neural networks. These assessments as well as certain user inputs such as gestational age are forwarded to a rule-based front end module, the purpose of which is to determine, based on the inputs from the first-stage classifiers and the user inputs, which of multiple classifiers in an outcome predictor module will analyze the fetal pattern. The rule-based front end selects a classifier in the outcome predictor and forwards the appropriate data to the selected classifier. The final classification of the data patterns is accomplished by one of the neural network classifiers in the outcome predictor module.

The outcome predictor module includes the multiple neural network classifiers which receive data patterns from the rule-based front end. Based on the input pattern, the appropriate classifier outputs a signal indicative of fetal condition or well-being. The signal classifies the fetal condition as being either normal, stressed, indeterminate or ominous and includes an associated probability. Other condition classifiers can also be used to indicate specific fetal states of interest. The output is received by a rule-based back end module of the expert subsystem. The module also receives the data selected by the rule-based front end for display to the clinician. The rule-based back end receives the data, the classification from the outcome predictor, the outputs of the first-stage classifiers and any user inputs and formats all of this data for presentation to the clinician on the system display.

Since the clinician is not likely to accept the classification by the expert subsystem without review of the data relied upon in making the classification, the data is available to the clinician on the system display. The display and storage subsystem organizes the data for display on the monitor, for printing on a strip chart and/or for storage in a data file.

In one embodiment, the screen display is divided into three windows. One of the windows acts like a strip chart to display important data as a function of time. A second window is a "smart" window in that what is displayed in the window is determined by the output of the classifiers in the expert subsystem. Based on the classification made by the expert subsystem, certain variables are automatically selected for display in the smart window with no intervention from the clinician, enabling the clinician to make an independent assessment of fetal condition using the displayed data. The third window is a text window which conveys information from the output of the classifiers, some summary data, the prediction of fetal well-being from the outcome predictor, and recommendations or warnings.

A number of predefined display configurations for all of the display windows are available. In addition, the user can define his/her own configurations. In another embodiment, the display capability of the monitor includes a real-time strip chart recorder. Thus, a hard copy record of pertinent data is available to the clinician for review.

In an alternative preferred embodiment of the invention, the display can present a three-dimensional plot of the TFR. The three-dimensional display preferably provides a visual interpretation of the fetal heart rate data as it is collected and processed. In one particular embodiment, the three-dimensional plot is updated with frequency-amplitude data at 1.0-second intervals. The visual display provides the clinician with the ability to quickly identify trends as well as transients in heart rate and heart rate variability to facilitate the conclusion as to fetal well-being.

Other signals such as the contraction signal and/or the fetal movement signal can be displayed with the three-dimensional TFR display. Alternatively, the three-dimensional TFR plot can be color coded to indicate conditions of the contraction and/or fetal movement signals. For example, during a contraction, the TFR plot can be produced in red, and, between contractions, it can be blue. This display format provides the clinician with a global view of how fetal heart rate variability is changing over time. In one preferred embodiment of the invention, the user has the option of reviewing the raw TFR data at any time or can substitute the three-dimensional TFR display for one of the three windows described above. Alternatively, the three-dimensional TFR display can replace all of the windows on the display.

Many realizations of the invention are possible. One such realization involves implementing the assessment process on a personal computer. In this embodiment, inputs to the computer are obtained from the outputs of various commercially available prior art monitors. An analog-to-digital board in the computer samples the heart rate time signal and the contraction and fetal movement signals if available. Calculations and analysis are performed on the computer by the various subsystems which can include a digital signal processing board and/or a neural network board and which are controlled by software running on a processor and stored in memory in the computer.

In another embodiment, the invention is a stand-alone device. The invention is implemented in hardware and/or software using a processor and memory inside the monitor.

The system of the invention provides numerous advantages over other devices. For example, as previously discussed, the use of a non-linear time-frequency representation allows for changes in heart rate variability to be located to specific periods of time. This improvement in time resolution allows the device to detect critical transient episodic fetal characteristics. This facilitates a much more informed decision as to overall fetal well-being.

The invention also combines the benefits of both rule-based classification and neural network classification. Initial classifications of data patterns are performed by rule-based classifiers to identify data pertinent to a particular fetal condition. These initial classifications allow the data pertinent to an indicated physical characteristic to be separated from the remaining fetal data.

The final assessment as to fetal well-being is performed by a neural network to eliminate certain drawbacks of rule-based final decision making. It has been shown through experiments that two experts can interpret the same fetal data as indicating different fetal conditions. In addition, it has also been shown that the same clinician can interpret the same data differently on different occasions. Since rules in a rule-based system must be compiled from experts, generating a library of rules for the rule-based system can be an inaccurate process given the disparity among expert opinions. In the present invention, the neural networks are "trained" on a database in which fetal well-being has been determined by objective criteria, e.g., by Apgar score, blood gas measurements and/or neural development. Thus, inaccuracies due to the nature of the process for extracting rules from experts for such a complex decision making task are eliminated.

It is also recognized that in a neural network based system, a clinician will not readily accept a final decision since the relationships among patterns developed by the neural network during training cannot be readily discerned from the network. Therefore, the basis for the classification of certain test data is unknown. The present invention presents on the display the data used by the neural network in its classification to allow the clinician to arrive at his/her own assessment without being required to rely on the classification made by the system of the invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 1A–1H contain time plots of variables showing a change in fetal state.

FIGS. 2A–2H contain time plots of variables showing fetal breathing efforts.

FIGS. 3A–3H contain time plots of variables showing fetal body movements.

FIGS. 4A–4H contain time plots of variables used to illustrate analysis of transient change in heart rate variability independent of changes in heart rate in the context of active labor during pushing.

FIGS. 7A and 7B contain time plots of heart rate and the contraction signal showing a sinusoidal variation in heart rate.

FIG. 8 is a top-level block diagram of the fetal data processing system of the invention.

FIG. 9 is a block diagram of the time-frequency representation subsystem of the invention.

DETAILED DESCRIPTION OF THE INVENTION

Figure 5A:
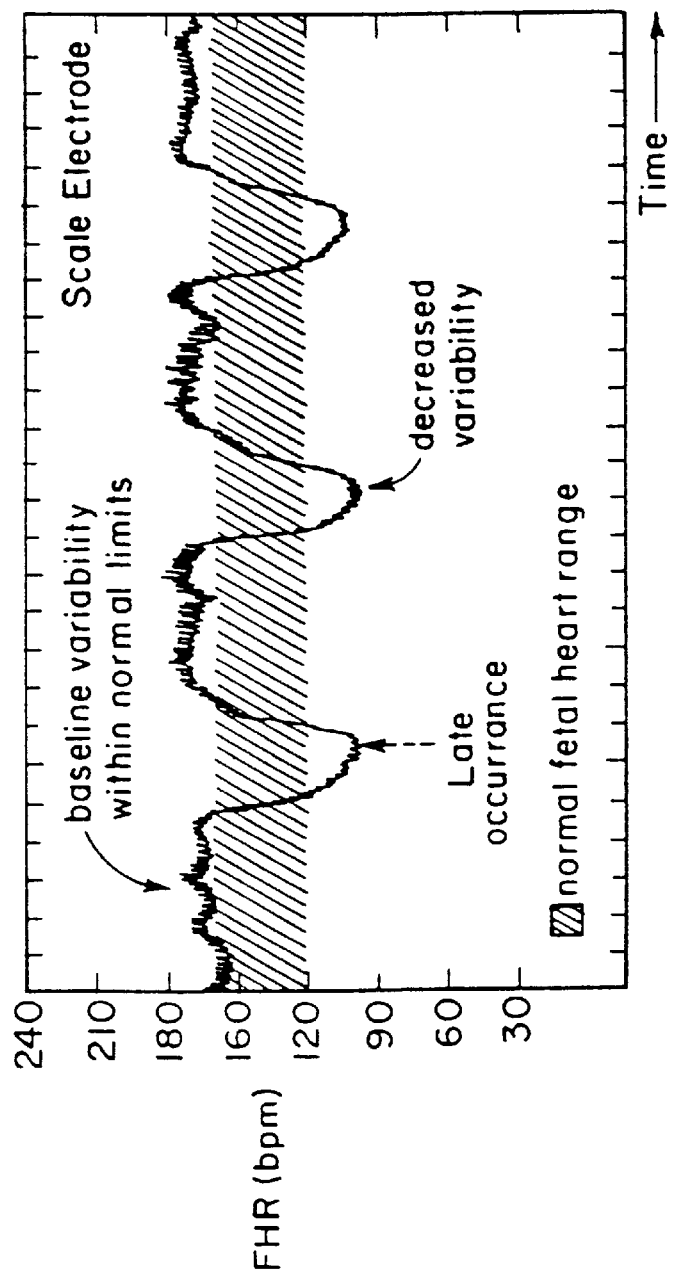
FIGS. 5A and 5B contain time plots of heart rate and the contraction signal showing a loss of variability during a deceleration.

In interpreting a fetal heart rate time trace, a clinician must make assessments concerning the baseline heart rate (HR) as well as the baseline variability of heart rate. In addition, clinicians must be able to classify transient changes in heart rate and heart rate variability (HRV) as to type and magnitude. These indices are important to the diagnosis of fetal distress. Optimal management of the stressed fetus also requires assessment of the progress over time of the fetal HR pattern as well as labor. Although determination of baseline HR is relatively straightforward from a standard fetal trace, quantitative assessment of HRV is more difficult. The present invention provides the clinician with a detailed, quantitative and continuous assessment of HRV. In addition, features important in assessing fetal well-being are continuously extracted and available for display to the clinician or as input to an expert subsystem in which an automatic assessment of fetal well-being is performed.

HR and HRV are controlled by the autonomic nervous system. The autonomic nervous system has two important branches; the sympathetic and parasympathetic nervous systems. Activation of the sympathetic nervous system elicits an increase in HR. Activation of the parasympathetic nervous system results in a decrease in HR. Since the influence of the parasympathetic nervous system on the heart is mediated exclusively by the vagus nerves, these effects are also referred to as vagal mechanisms. The effects of alter autonomic tone on HRV is complex and much information has been obtained in the adult by use of spectral analysis.

It has been determined that if one examines HRV in the frequency domain as a spectral plot of amplitude versus frequency, variation in HRV at frequencies above 0.15 Hz are due to parasympathetic, i.e., vagal, mechanisms. Typically, there is a peak in the amplitude spectrum at about 0.25 Hz, the typical frequency of breathing, corresponding to respiratory modulated changes in HR. These changes in HR are mediated exclusively by parasympathetic mechanisms. Typically in the adult, two or more peaks can be detected in the amplitude spectrum at frequencies below 0.25 Hz. These are mediated by both sympathetic and parasympathetic mechanisms. Changes in the control of the heart by the autonomic nervous system are reflected by changes in the frequency domain description of HRV. For example, patients with congestive heart failure have a decreased amplitude spectrum. In addition, an orthostatic stress such as tilt will cause an activation of arterial baroreceptors which will increase sympathetic and decrease parasympathetic activities. The amplitude spectrum will exhibit a decrease in high frequency activity, but an increase in low frequency consistent with the changes in autonomic nervous system activity.

The present invention applies frequency domain techniques to fetal assessment. However, the techniques commonly used in the adult cannot be applied to the analysis of fetal HRV since these methods require that the signal be stationary, i.e., that the characteristics of the patient do not change over the period of analysis. The characteristics of the fetus are changing, often over very short periods of time. These changes can be due to alterations in sleep state, periodic stress induced by uterine contractions, and fetal body and breathing movements, both of which are highly variable and episodic in nature. In addition, there is information crucial to the assessment of fetal well-being in these transients and nonstationarities.

As will be described below in detail, the system of the invention receives a heart rate time series obtained from another monitor or from an internal monitor. The signal is first high-pass filtered, removing the DC and very low frequency components. The signal is then made analytic by a Hilbert Transform, and a non-linear time-frequency representation (TFR) of the signal is calculated on a point-by-point basis.

In order to present the TFR to the clinician in a concise and meaningful way, the area under the amplitude-frequency plot is calculated over specified frequency bands. These areas are then output for display. As an example, the frequency bands can be defined as follows:

$A_{HF}$: High Frequency (HF) 0.50–1.1 Hz $A_{MF}$: Mid frequency (MF) 0.15–0.50 Hz $A_{LF}$: Low frequency (LF) 0.02–0.50 Hz The MF and HF band are modulated solely by the parasympathetic nervous system since sympathetic modulation of HR is minimal above 0.15 Hz. When episodic fetal breathing efforts occur, the frequency of breathing is typically 0.5 to 1.0 Hz. Thus, any vagally mediated modulation of HRV by breathing efforts is demonstrated in the high frequency band. The LF band should reflect both sympathetic and parasympathetic modulation of HRV, and includes contributions from baroreceptors, fetal body movements, and temperature regulation systems.

Total area $A_T$ under the amplitude-frequency curve from 0.02 to 1.1 Hz is a measure of overall HRV. The sum $A_{MH} = A_{MF} + A_{HF}$ provides a measure, although incomplete, of vagal modulation. The ratio $A_R = A_{MH}/A_{LF}$ provides an index of overall sympatho-vagal balance. Also defined is the ratio $A_B = A_{HF}/A_{MF}$. The variables $A_{LF}$, $A_{MF}$, $A_{HF}$, $A_T$, $A_{MH}$, $A_B$ and $A_R$ are available for continuous display on the display of the monitor. These area variables are referred to collectively herein as $A_X$, where $X \in \{LF, MF, HF, T, MH, B \text{ and } R\}$.

It will be understood that the frequency bands listed above, as well as the total frequency range, are used for illustration purposes only and not as limitations. Other frequency bands and ranges can be used. The definition of the frequency bands are based on current understanding of the physiology. These are envisioned as the default definitions. The user is able to enter new values for the frequencies defining the bands or even change the number of bands analyzed. In addition, the user has the capability of defining ratios and/or sums of pairs of areas.

Analysis of the computed areas, the HR trace and HRV indicates fetal characteristics which in turn indicate overall fetal well-being. That is, certain specific data patterns identify specific associated fetal characteristics or activities. These characteristics or activities include change of state, breathing efforts, fetal body movements, transient changes in HRV, HR deceleration and acceleration, and sinusoidal variations in HRV. This list is not intended to be exhaustive as numerous other fetal characteristics can be identified by analyzing data. To demonstrate the assessment process of the invention, some examples of the application of the TFR to fetal HRV will now be described.

Changes in state. It has been shown by experiment and described in the literature that after approximately 36 weeks, most fetuses show evidence of organized behavioral states. Two stages of sleep as well as wakefulness can be discerned in instrumented lamb fetuses. In the human fetus, there are four states which can be identified by a HRV pattern, the two most common of which are 1 F and 2 F. State 1 F is a low variability state, and 2 F is a high variability state. A change between state 1 F and 2 F can be discerned from HRV, and in order to distinguish a change in state from other short-term transients, a change in HRV must be sustained for a number of minutes; typically, 3–5 minutes have been used in the literature.

Shifts between states 1 F and 2 F can be discerned from TFR analysis by monitoring $A_T$ as a function of time. An example is shown in FIGS. 1A–1H. A low variability state may indicate either fetal distress or simply state 1 F. Therefore, it is important to have the capability of determining the duration of states. A normal fetus will cycle between states typically at intervals of approximately 30 minutes. As the duration of a low variability state exceeds 30 minutes, the likelihood that the pattern indicates a distressed fetus increases.

Detection of Fetal Breathing Movements. Breathing movements in the fetus are episodic, i.e., they occur in bursts, each lasting from tens of seconds to a couple of minutes. The frequency of occurrence of fetal breathing episodes varies with state, gestational age, labor, and fetal distress. Therefore, the ability to obtain an index which could provide information as to the occurrence of fetal breathing efforts aid the clinician in evaluating fetal well-being.

During an episode of breathing movements, the frequency of breathing typically ranges from 30 to 60 per minute (0.5 to 1.0 Hz). Therefore, the direct effects of breathing efforts on HRV would be expected to be manifested in the HF range of the TFR. An example of a change in HRV consistent with an episode of fetal breathing is shown in FIGS. 2A–2H. At approximately minute 13 there is an increase in $A_{HF}$, lasting approximately 30 seconds. There is also an increase in the $A_R$ ratio indicating a preferential increase in HF vagal modulation consistent with an episode of fetal breathing. Close examination of the HR trace reveals the presence of a high frequency variation. However, the presence of this high frequency transient is more apparent from the $A_{HF}$ trace compared to the original HR trace.

Effects of Fetal Body Movements. After 28 weeks gestation, fetal body movements are typically accompanied by changes in HR. Increases in HR with body movements usually indicate a reactive fetus and is considered a sign of fetal well-being. It has been shown that the exact morphology of the change in HR which accompanies fetal body movements depends on the pattern of fetal movement. Slow trunk rotations are associated with slow increases in HR. The stronger the body movement, the greater the change in HR. Complex body movement patterns, such as arms with trunk rotation, produce a more complex HR pattern, e.g., the acceleration may be interrupted by brief decelerations. These changes in HR would produce consistent changes in the TFR over time. Changes would be expected predominately in $A_{LF}$ for slow changes, whereas for more complex changes in HR associated with more complex patterns of body movements would be associated with changes in other frequency bands. In addition, increased magnitude of changes in HR with body movements would be reflected by a greater value in the appropriate frequency band.

An example of HRV analysis in a fetus during the early stages of labor is shown in FIGS. 3A–3H. There are episodic changes in HR which are not associated in a consistent fashion with contractions. Thus, these likely represent the response to fetal body movements. Differences in the morphology of the HR changes can be discerned from the response of the TFR parameters. For example, the HR transient at 2 minutes is slow as evidenced by the dominant peak in $A_{LF}$, whereas the transient at 8 minutes is predominately a higher frequency transient as seen by the dominate peak in $A_{MF}$. Thus, the application of the TFR to the fetal HR allows the monitor not only to identify but to characterize in more detail the HR transient.

Transients in HRV. There are times when there may be clear changes in HRV without concomitant changes in HR. These changes may reflect accelerations or decelerations as usually defined in the literature or they may reflect other events. FIGS. 4A–4H present the results of HRV analysis obtained from a patient late in labor while pushing. Although there are no consistent changes in the level of HR with each push, there are reproducible changes in the parameters related to HRV. There is an increase in HRV in all frequency bands with each episode of pushing. This suggests that the fetal autonomic nervous system is responding to the increased intrauterine pressure, which in turn suggests that the fetus is reactive. Such reactivity is a positive sign of fetal well-being. The ability to make this assessment may be particularly important in this fetus since baseline variability, variability between the contractions, is quite low which could indicate either fetal distress or behavioral state 1 F. Other systems for HR monitoring during labor do not examine transients in HRV independent of changes in HR.

Analysis of Decelerations. One of the most common diagnostic patterns of fetal HR during labor is that of decelerations, i.e., a decrease in HR which is coupled to contractions. First, decelerations are typically classified by shape, either uniform or variable. Uniform decelerations are characterized by a similar shape having gradual onsets and offsets. However, if the shape of decelerations varies from one to the next, they are considered variable decelerations. Based on the relationship between the timing of the occurrence of the decelerations and contractions, uniform decelerations are usually further subdivided into early and late decelerations. Early decelerations start with the onset of the contraction. The minimum HR occurs at the peak of the contraction and the decrease in HR from baseline is modest. It is thought that these decelerations are reflex mediated, indicating a reactive fetus and are, therefore, not ominous. However, it is very important to distinguish early decelerations from either late or variable decelerations.

Late decelerations are delayed in time relative to the contraction and the minimum HR occurs after the peak of contraction. In general, late decelerations are thought to be due to hypoxia. If HRV is good, the hypoxia can often be helped by maternal hyperoxia or repositioning. Late decelerations with decreased variability are associated with an increased incidence of fetal acidosis and low Apgar score.

The Apgar score results from an examination of the newborn shortly after birth. The physician or nurse evaluates the newborn's heart rate, respiratory effort, muscle tone, reflex irritability and skin color. A score of either 0, 1, or 2 is given for each of the five variables determined by a simple set of well-known criteria. A score of 10 indicates a vital newborn whereas a score less than 7 usually indicates a depressed infant which may need resuscitation. Typically, the Apgar score is obtained at 1 and 5 minutes after birth.

Variable decelerations vary in appearance and temporal relationship to contractions. The first step in classifying variable decelerations is to make a determination of size. This includes measures of absolute depth as well as duration. The next step in classification of variable decelerations involves determining if classic features are preserved or whether atypical features are superimposed. Because of the number of different mechanisms affecting decelerations, variable decelerations can be associated with the complete spectrum of fetal well-being, from a healthy to a moribund fetus.

Figure 5B:
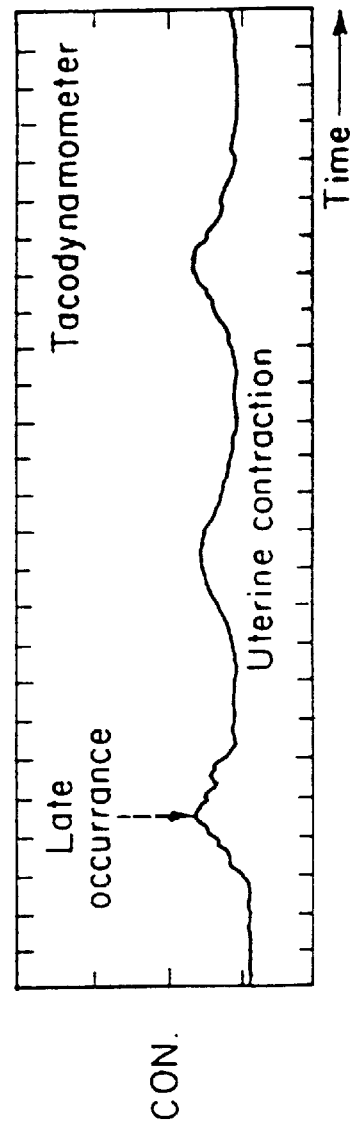

There are seven atypical features which may be associated with variable decelerations. The most ominous of these is a loss of variability during the deceleration as shown in FIGS. 5A and 5B. FIGS. 5A and 5B are a time plot of the baseline HR signal and the uterine contraction signal. The baseline HR signal shows decelerations associated with contractions and loss of heart rate variability during the decelerations. Because of its increased time resolution, the TFR technique of the invention allows quantification of the loss of variability and the localization in time of such a loss, i.e., at the nadir of the deceleration or during recovery, etc. This cannot be accomplished using prior standard spectral techniques.

The six remaining atypical features will be briefly described. 1) Loss of primary acceleration is the most frequently encountered atypical feature. Nearly one third of the infants born with this atypical feature have an Apgar score less than 7 at 1 minute. However, less than 7% of these infants have an Apgar less than 7 at 5 minutes. 2) Loss of secondary acceleration is the third most common atypical feature and is of slightly more concern than the loss of primary acceleration. 3) A slow return to baseline HR occurs in 60% of atypical variable decelerations and is associated with a 1 minute Apgar score less than 7 in 47% of fetuses and a 5 minute Apgar less than 7 in 10% of the fetuses. 4) A prolonged secondary acceleration is thought to be due to hypoxia possibly indicating an abnormal umbilical cord position. 5) A biphasic deceleration is characterized by an initial deceleration, a return towards baseline, followed by a second deceleration. Thus, the HR trace resembles a W. This is the fifth most commonly occurring atypical feature. When present, the incidence of an Apgar score less than 7 at 1 minute is 48%, while the incidence of an Apgar score less than 7 at 5 minutes is 12%. 6) The least common atypical feature is a continuation of baseline at a lower level, i.e., there is a deceleration and HR returns to a level below the original baseline. While the presence of this feature predicts an Apgar less than 7 at 1 minute in 43% of the fetuses, only 7% will have an Apgar less than 7 at 5 minutes.

Figure 6:
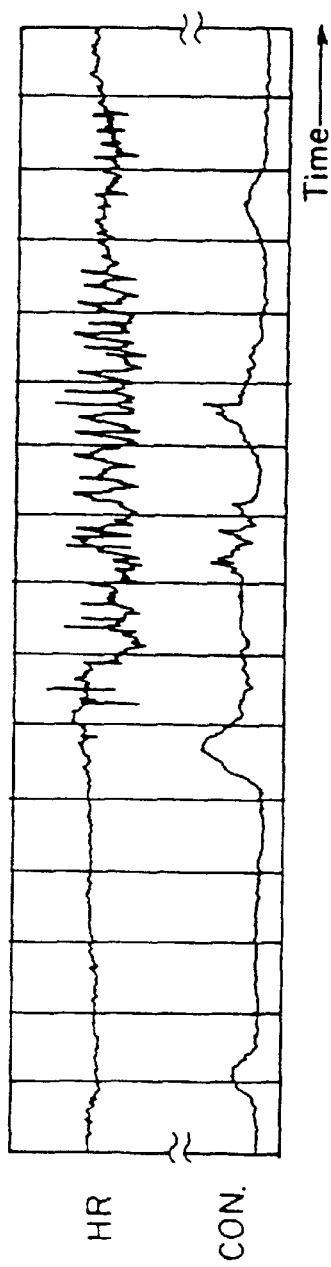
FIG. 6 contains time plots of heart rate and the contraction signal showing a period of increased heart rate variability.

Periods of Increased HRV. Increases in HRV are often associated with hypoxia and, in general, represent normal compensatory mechanisms of a reactive fetus. The occurrence of such a stress pattern can serve as an alert to the onset of fetal hypoxia, which should then be monitored to insure that it does not progress to a distress pattern. Shown in FIG. 6 is an example of increased HRV in a term fetus. In this particular case, the hypoxia is likely due to the increased uterine activity as evidenced by an increased baseline tone and a lack of a resting phase.

Marked Sinusoidal Pattern. Many cases of pure sinusoidal pattern reflect a benign fetal response secondary to a drug effect. However, sinusoidal patterns may also be due to severe fetal anemia or perinatal asphyxia. For the latter case, a sinusoidal pattern is particularly ominous and is consistent with severe fetal jeopardy. An example of a marked sinusoidal pattern is shown in FIGS. 7A and 7B.

A sinusoidal HR pattern can be detected by examining each TFR for a dominant peak at a frequency of about 1 cycle per 2–5 minutes. One of the difficulties in identifying a sinusoidal pattern is to distinguish it from an undulating, but not sinusoidal, pattern. This can be done by examining the higher harmonics. The value of the TFR at the higher harmonics can be relatively larger for an undulating pattern compared to a true sinusoidal pattern.

It is important to know how changes in HR and HRV are affected by uterine contractions. Therefore, the time of occurrence and magnitude of the peak of uterine contraction, the duration of the contraction, the interval between successive contractions, and baseline level of the contraction signal will all be estimated. The source of the contraction signal (CON) can be an external tocodynamometer or an interuterine pressure transducer.

Also, many new fetal monitors have the ability to detect fetal movements. A fetal movement signal (FM) is analyzed for number of movements and the time of occurrence of movements. Classifiers included in the expert subsystem of the monitor will correlate changes in variability with the fetal movements.

A top-level block diagram of the fetal data processing system 10 of the invention is shown in FIG. 8. There are four major subsystems in the system 10: 1) a time-frequency representation (TFR) subsystem 12 for performing the time-frequency transformation to calculate the nonlinear TFR of heart rate, 2) a feature extraction subsystem 14 for extracting and compiling pertinent data features from all of the input fetal data, 3) an expert subsystem 16, and 4) a display and storage module 18. The only required input to the system is the HR time series, generated by either another monitor or software module or by an internal monitor or software module. Optional inputs to the system 10 include signals related to the strength of contraction (CON) and fetal movements (FM). The system 10 adjusts the extraction of features as well as the assessment by the expert subsystem 16 as a function of the presence or absence of these optional inputs.

Each of the subsystems shown in FIG. 8 will now be described in detail. A block diagram of the TFR subsystem 12 is shown in FIG. 9. The input to this subsystem is the HR time series. Initially, the HR time series is filtered by a digital highpass filter 20 to remove the DC and very low frequency components of the signal. The exact form of the digital high pass filter 20 is not critical, having only the requirement that the magnitude characteristic be monotonic over the pass band. The cutoff band is currently set to 0.06 Hz., i.e., frequency components below this are attenuated. This value was arrived at empirically and might be altered in subsequent realizations.

The filtered heart rate signal is then made analytic by a digital Hilbert Transformer 22. Alternatively, the HR time series could be made analytic using FFT techniques, but this would introduce delays into the processing and is, therefore, not the preferred implementation.

The non-linear TFR is then calculated on the analytic heart rate signal. Preferably, this is accomplished using a non-linear transformation such as a smoothed Wigner distribution 24, although other specific implementations of the TFR, such as the Choi-Williams distribution, can also be used. A smoothed version of the Wigner distribution is calculated as:

$$W(n, m) = \frac{1}{2}N \sum_{k=-N+1}^{N-1} |h(k)|^2 \left[ \sum_{p=-M+1}^{M-1} g(p)x(n+p+k)x^*(n+p-k) \right] e^{-2i\pi m/N}$$

where x is the analytic heart rate signal, g(p) is a time domain smoothing function, h(k) is a symmetric normalized frequency domain window function. In the present implementation, g(p) and h(k) are rectangular and Gaussian windows, respectively; although other windows could be used. The details of the non-linear transformation are described in "Linear and Quadratic Time-Frequency Signal Representations," by F. Hlawatsch et al., *IEEE Signal Processing Magazine*, pp. 21–67, (April, 1992), the contents of which are incorporated herein by reference.

The input to the area calculation module 26 is the TFR W(n,m). The areas under the amplitude-frequency plot are calculated over the frequency bands specified above. The outputs of the module 26 are: $A_{LF}$, $A_{MF}$, $A_{HF}$, $A_{MH}$, $A_R$, $A_B$, and $A_T$. These are collectively referred to herein as $A_X$.

Figure 10:
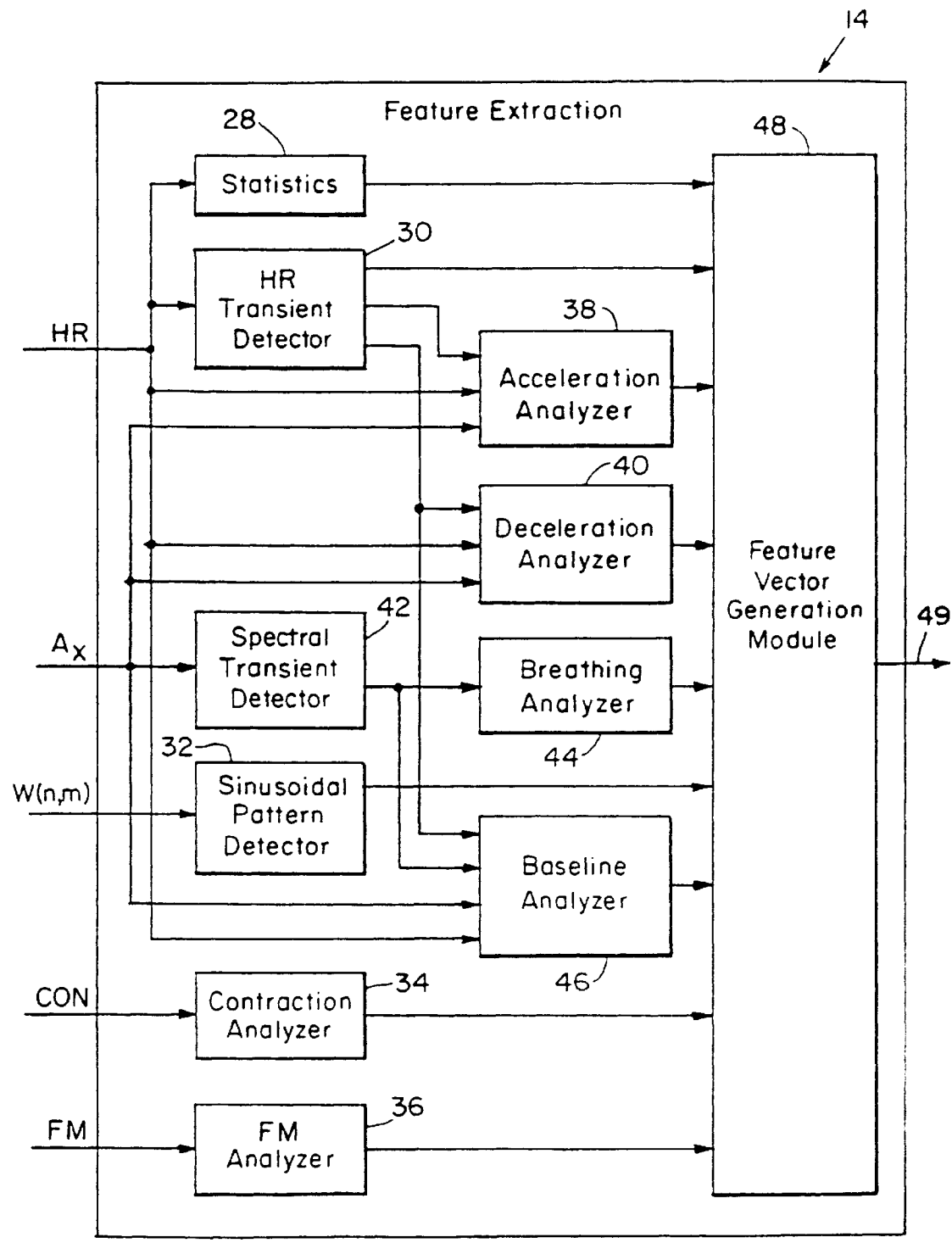
FIG. 10 is a block diagram of the feature extraction subsystem of the invention.

A block diagram of the feature extraction subsystem 14 is presented in further detail in FIG. 10. The purpose of this subsystem is to calculate and/or identify and extract important variables or features from the HR time series, the TFR, the calculated areas, the contraction signal, and the fetal movement signal. The subsystem 14 then gathers pertinent items of data and compiles them into a feature vector.

The required inputs to the feature extraction subsystem are the HR time series, the TFR of the HR signal (W(n,m)), and the areas calculated from the TFR. Optional inputs include the contraction signal and the fetal movement signal. By making a number of inputs optional, the number of environments in which the monitor can be used is increased. Thus, in the antepartum environment, having a HR time series may be sufficient for an initial screening of fetal status. However, accurate determination of fetal status during active labor requires a signal indicative of uterine activity. The function of each module within the subsystem 14 will now be described.

In the statistics module 28, time domain indices of average heart rate and variability are calculated over one-minute blocks. Since occasional transient artifacts are likely in the HR time series, these indices should be robust in the presence of such artifacts. Thus, the median heart rate and the inner first quartile range are used. To do this, all values of HR over the one-minute block are ranked from low to high. The median HR, $HR_M$, is defined as the HR at which 50% of the values are lower and 50% of the values are higher. The inner quartile HR range, $HR_Q$, is defined as the difference between the value of the HR at 12.5% above the median minus the value of the HR at 12.5% below the median.

The input to the HR transient detector module 30 is the HR time series. This module 30 detects the occurrence of a transient in HR, either an acceleration or a deceleration. The change must be greater than a predefined threshold, $\delta_{HR}$, and have a minimum duration, $\tau_{HR}$. The outputs of the module 30 are an identification of the type of transient (acceleration or deceleration) and the times of occurrence of the beginning and end of the transient, $T_{Ts}$ and $T_{Te}$, respectively.

In the sinusoidal pattern detector 32, a sinusoidal heart rate pattern is detected by examining the TFR for a dominate peak. The dominate peak will be at the fundamental frequency of oscillation. A purely sinusoidal pattern would have a single peak at the frequency of oscillation. More complex patterns of oscillation would have significant peaks at higher harmonics. As an index of how closely the HR pattern resembles a pure sinusoid, the ratio of the amplitudes of the TFR at the fundamental and first harmonics will be calculated, i.e., $S_R = TFR(f_0)/TFR(2f_0)$, where $f_0$ is the fundamental frequency of oscillation. A HR pattern will be considered sinusoidal if $S_R$ is greater than a threshold $\delta_S$.

The contraction analyzer 34 will be invoked if the contraction signal CON is being analyzed. This module 34 detects the following parameters from the contraction signal: time of peak contraction $T_{Cp}$; peak magnitude $C_p$; time of start of contraction $T_{Cs}$; time of end of contraction $T_{Ce}$; and baseline magnitude $C_B$. If the contraction signal is from a tocodynamometer, the values of the start and end points as well as the magnitudes will only be approximate due to inaccuracies in the sensor methodology. However, if the contraction signal is obtained from an interuterine catheter, these values will be accurate.

The input to the fetal movement analyzer 36 is the fetal movement signal. The analyzer 36 detects the occurrences of movements and record a time for each occurrence.

The inputs to the acceleration analyzer 38 are: 1) the times for the start and end of an acceleration, $T_{As}$ and $T_{Ae}$, respectively, obtained from the HR transient detector module 30, 2) the areas calculated from the TFR curve by the area calculation module 26, i.e., $A_{LF}$, $A_{MF}$, $A_{HF}$, $A_{MH}$, $A_R$, $A_B$ and $A_T$, and 3) the HR time series. The peak HR during the acceleration, $HR_A$, and the duration of the transient are calculated from the input data.

Figure 11:
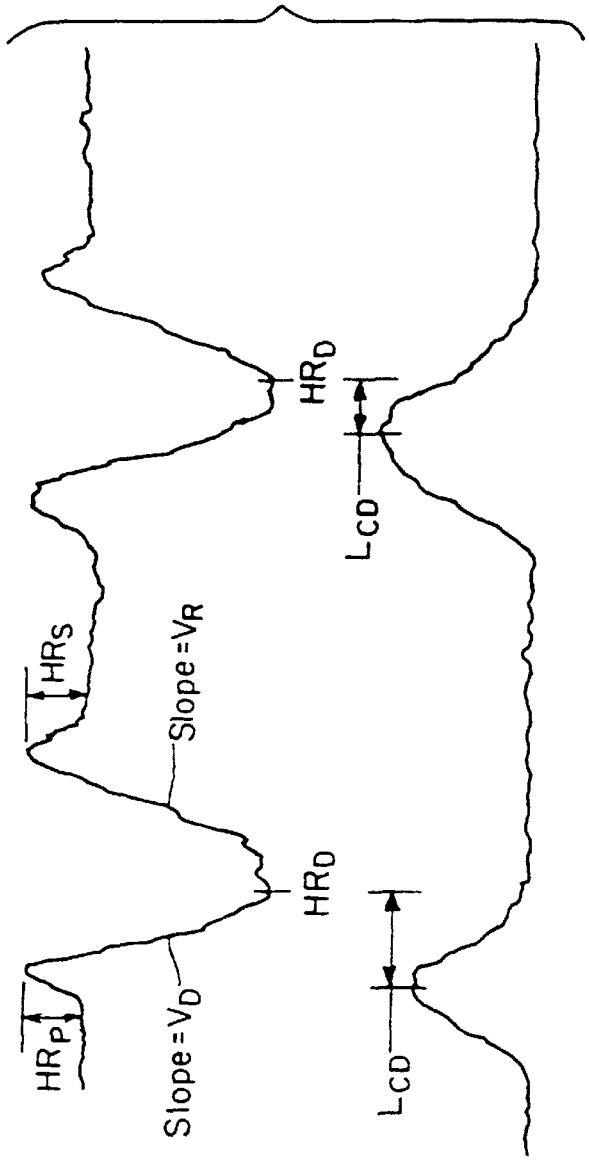
FIG. 11 contains schematic time plots of the heart rate signal and contraction signal illustrating the definition of certain variables used by the system of the invention.

The inputs to the deceleration analyzer 40 are 1) the times for the start and end of deceleration, $T_{Ds}$ and $T_{De}$, respectively, obtained from the HR transient detector 30, 2) the areas calculated from the TFR curve by the area calculation module 26, i.e., $A_{LF}$, $A_{MF}$, $A_{HF}$, $A_{MH}$, $A_R$, $A_B$ and $A_T$, and 3) the HR time series. The following variables are calculated from the input data: minimum HR during deceleration $HR_D$; lag from peak contraction to minimum HR, $L_{CD}$; velocity of decline for HR, $V_D$; velocity of recovery for HR, $V_R$; magnitude of primary acceleration $HR_P$; and magnitude of secondary acceleration $HR_S$. The definition of these variables is illustrated in FIG. 11 which shows time plots of the HR time series and the contraction signal.

In addition, changes in the spectral indices during the deceleration are also calculated. These will be calculated as changes from baseline and will be calculated for two time points during the deceleration, vis., at the nadir and during recovery. These will be designated as $A_{Xn}$ and $A_{Xr}$, respectively, where $X \in \{LF, MF, HF, MH, R, B, T\}$.

Changes in HRV can occur without either substantial or sustained changes in HR. Therefore, it is important to also detect transients in HRV. In the monitor of the invention, the variables output from the area calculation module 26 are examined for transients in the spectral transient detector module 42. A change in a variable will be considered significant if it exceeds a threshold, $\delta_X$, and is maintained for a minimum period of time, $\tau_X$. The following variables will be calculated and output by the module 42: time of transient onset $T_{Xo}$; duration of transient $\Delta_{XD}$; time of peak change, $T_{Xp}$; peak magnitude, $A_{Xm}$; where X is an element of {LF, MF, HF, MH, R, T}.

Fetal breathing movements are episodic. During a period of fetal breathing movements, the frequency of breathing effort is usually between 0.7 and 1.1 Hz. Thus, changes in HR associated with the respiratory efforts will have a component in that frequency range. This will be manifested by a preferential increase in $A_{HF}$ and, therefore, an increase in $A_B = A_{HF}/A_{MF}$. As described above, an example of breathing modulated changes in HRV are shown in FIG. 2.

The inputs to the breathing analyzer 44 are the outputs of the spectral transient detector module 42. A breathing episode will be defined by preferential increases in $A_{HF}$ and $A_B = A_{HF}/A_{MF}$ above thresholds $\delta_{HF}$ and $\delta_B$, respectively, having a minimum duration $\tau_{HF}$ and $\tau_B$, respectively. The output of this module 44 is the time of the start and end of the breathing episode, $T_{Rs}$ and $T_{Re}$, respectively.

The inputs to the baseline analyzer module 46 include outputs of the HR transient detector 30 and spectral transient detector 42 modules as well as the calculated areas and the HR time series. These inputs are used to identify periods without transients either in HR or in spectral variables. Updated baseline values for HR and spectral variables will be averaged over a window, where the minimum window length is 30 seconds. Outputs from the module 46 include: median HR, $HR_{Mb}$; inner quartile range, $HR_{Qb}$; and the spectral indices averaged over the window, $A_{Xb}$, where X={LF, MF, HF, MH, R, T}.

All of the data outputs from the various modules within the feature extraction subsystem 14 are received by a feature vector generation module 48. The module 48 compiles the data and generates a feature vector or matrix which contains all of the data items used by the monitor 10 to perform the fetal assessment process. The feature vector is updated each time the HR time series is sampled to generate a new TFR and is output from the feature extraction subsystem 14 as shown at 49.

Figure 12:
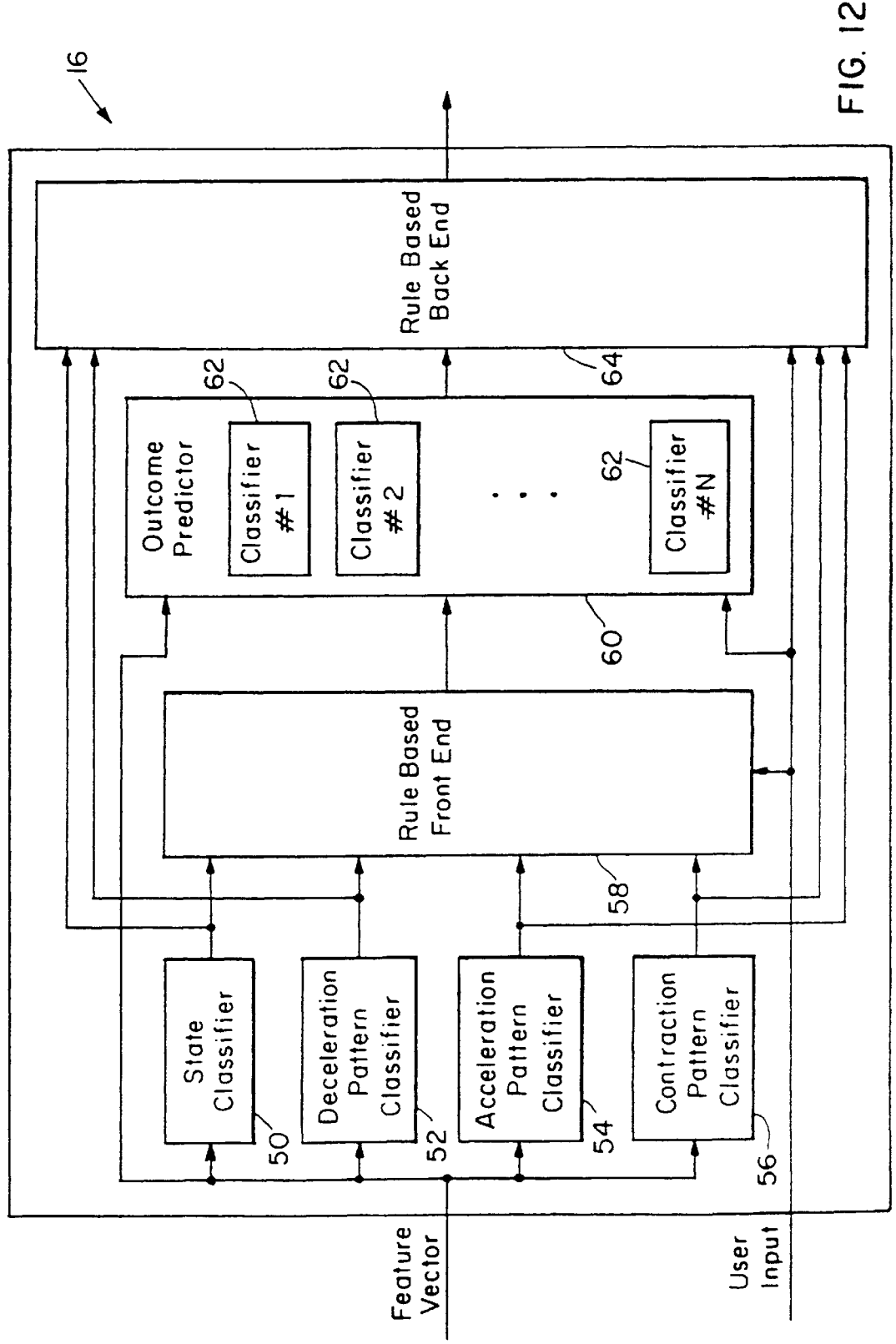
FIG. 12 is a block diagram of the expert subsystem of the invention.

A block diagram of the expert subsystem 16 is shown in FIG. 12. The principal function of the expert subsystem 16 is to make an assessment of fetal well-being based on the features being presented to it in the feature vector by the feature extraction subsystem 14 as well as user input.

The expert subsystem 16 is a "hybrid" expert system, i.e., it contains both standard rule-based modules as well as neural networks. Previous attempts at designing expert systems for the evaluation of fetal well-being have been exclusively rule-based. However, there are inherent limitations in such an approach. First, it requires that the "rules" used by the "expert" or the clinician be accurately and completely extracted and then implemented. Second, an expert must be identified. Evidence suggests that it is not possible to accomplish these two goals since the variability between experts in assessing the same fetal tracings is quite high and the variability in the assessment of the same fetal trace by a single expert at different times is surprisingly high. In addition, the modification and maintenance of a solely rule-based expert system is labor intensive.

An alternative approach is to take all the relevant variables and apply them as inputs to a neural network and train the network to recognize patterns associated with good outcomes and bad outcomes. The fundamental limitation of such an approach is that with current technology it is not possible to determine from the network how the network arrived at its conclusion. This would not be accepted by the clinician.

The approach taken in the current invention is to break down the analysis of the fetal tracings into a number of tasks that follows classical clinical paradigms. Each task may be accomplished using a rule-based system or a neural network. In the current configuration, prediction of fetal outcome and the final decision as to overall fetal well-being are performed by one of a series of neural networks.

Proper assessment of overall fetal well-being by analysis of HR and HRV requires that certain confounding issues be accounted for. Four variables, state, deceleration pattern, acceleration pattern and contraction pattern, must be assessed from the feature vector, while other variables such as gestational age must be input by the user. The expert subsystem 16 includes four first-stage classifiers which analyze the feature vector for the four variables.

The state classifier 50 is a rule-based classifier which assigns a behavioral state to the fetus. The convention of defining behavioral state will be taken from "Are There Behavioral States in the Human Fetus?" by J. G. Nijhuis et al. in Early Human Development, Volume 6, pp. 177–195, 1982, which is incorporated herein by reference. Thus, possible classification states include 1 F, 2 F, 3 F, 4 F, and indeterminate. Briefly, the corresponding heart rate patterns associated with each state will be described. State 1 F is characterized by a stable heart rate with relatively low variability. There can be isolated accelerations associated with fetal movements. In state 2 F, there is a much increased HRV with frequent accelerations. In state 3 F, HRV is increased compared to 1 F, but, unlike 2 F, there are no accelerations. In state 4 F, HR is unstable with large, prolonged accelerations which commonly are fused into a sustained tachycardia. States 1 F and 2 F are the most commonly observed.

Updating of state classification will occur every $T_S$ seconds. In one embodiment, a default value for $T_S$ is 60 seconds, but that can be changed by user input. If no periodic decelerations have been detected by the feature extraction subsystem 14, then determination of state will be made from time domain and spectral indices of HRV from the last $T_S$ seconds. In the case of decelerations, time domain and spectral indices obtained from the baseline analyzer 46 will be used. Initially, HRV indices will be compared to population statistics for classification of state. If however, a new state has not been identified after a period $T_D$, the last $T_D$ minutes of data will be examined for relative changes. In one embodiment, a default value for $T_D$ is 30 minutes, but that can be changed by user input. One possible circumstance that must be taken into account is that, in a depressed fetus, a change from a low variability state to a relatively high variability state may occur, but the HRV during the high state may be lower than the value obtained from a population of healthy fetuses. It is important that the change in state be noted, since a fetus which is changing states is healthier than one who is not.

The purpose of the deceleration pattern classifier 52 is to make an initial classification of the overall deceleration pattern as being early, late, variable, late/variable or prolonged. The classifier 52 will analyze data over a window of a present number $L_C$ of contractions. In one embodiment, a default number of contractions $L_C$ is five. The user can change this number as desired. Update in classification can occur with each new contraction. The classifier 52 will use the following data from the feature vector to make its classification: $L_{CD}$, $T_{Ts}$, $T_{Te}$, $V_D$, $V_R$, $HR_P$, $HR_S$ and $HR_D$. This classifier is preferably rule based but could be a neural network.

The purpose of the acceleration pattern classifier 54 is to make an initial classification of the acceleration pattern as being nonperiodic, periodic or prolonged. The classifier 54 will analyze data over a window of $L_C$ contractions. Update in classification can occur with each new contraction. The classifier 54 will use the data $HR_A$, $T_{Ts}$, and $T_{Te}$ from the feature vector to make its classification. This classifier is preferably rule based but could be a neural network.

The purpose of the contraction pattern classifier 56 is to analyze uterine activity. This classifier 56 will only be active if a contraction signal is present. The details of the operation of the classifier will depend on whether an internal or external uterine monitor is being used. The classifier will use the following data from the feature vector: $T_{Cp}$, $C_p$, $T_{Cs}$, $T_{Ce}$, and $C_B$. The classifier will use data from the past Lp contractions and update its classification with each new contraction. In one embodiment, the default number of contractions $L_p$ is set at seven. However, this number can be varied by the user. The contraction pattern will be classified as normal, increased activity, decreased activity or discoordinate activity. This classifier is preferably rule based but could be a neural network.

To summarize the operation of the four initial classifiers 50, 52, 54, 56, each will extract variables from the feature vector appropriate for its classification task, use rules to determine its output, and output a single variable. The possible values of the output of each classifier is summarized as follows:

1) state classifier: 1 F, 2 F, 3 F, 4 F, indeterminate;
2) deceleration pattern classifier: early, late, variable, late/variable, prolonged, none;
3) acceleration pattern classifier: nonperiodic, periodic, prolonged, none;
4) contraction pattern classifier: normal, increased activity, decreased activity, discoordinate activity.

The classification of the HR and HRV patterns into either healthy or ominous must take into account the context of the situation. For example, it is important to know the gestational age of the fetus, the present state of the fetus, and the state of labor and other variables.

The final classification of the HR and HRV pattern will be accomplished by one of a series of available classifiers 62 in the outcome predictor module 60. The purpose of the rule-based front end 58 is to determine based on inputs from the first-stage classifiers 50, 52, 54, 56 and data entered by the user which of the available classifiers 62 will analyze the fetal pattern. The rule-based front end will also determine which inputs are extracted from the feature vector and presented to the selected neural network. As an example, if the outputs of the first four classifiers were 1 F (state classifier), variable (deceleration pattern classifier), none (acceleration pattern classifier), and normal (contraction pattern classifier), a specific neural network based classifier 62 would be selected, and the appropriate data would be extracted from the feature vector. If, however, the outputs of the first four classifiers were 1 F, none, none, normal, a different neural network classifier 62 would be selected to predict fetal outcome, and a different set of variables would be extracted from the feature vector as input to the different network.

The outcome predictor module 60 consists of a series of N classifiers 62, each of which can preferably include a neural network. The classifier 62 which performs the outcome prediction is selected by the rule-based front end module 58. Inputs to the outcome predictor 60 include data from the feature vector, user input, and outputs from the first-stage classifiers 50, 52, 54, 56. The selected classifier 62 will use data from the previous $N_p$ minutes and will update its classification every $N_u$ minutes. In one embodiment, default values for the time periods $N_p$ and $N_u$ are 30 minutes and 10 minutes, respectively. Both of these values can be varied by the user.

The output of the outcome predictor 60 classifies the overall fetal well-being as either normal, stressed, indeterminate or ominous. The output classification also includes an associated probability.

Each classifier 62 includes two parts, a preprocessor and neural network. The preprocessor extracts the correct data from memory and normalizes each variable. The purpose of the latter function is to ensure that each input to a neural network has a value between −1 and 1. Once the data has been extracted and normalized, the neural network is invoked and the classification of fetal well-being is then made.

The precise structure of each neural network will vary from classifier to classifier. The aspects of the neural networks common to all classifiers will now be described. In one embodiment, the basic structure of the neural network is a three-layer feed-forward network with full interconnections trained using back propagation techniques. The first layer is an input layer, the second layer is a hidden layer, and the third layer is an output layer. Each neuron in the input layer receives a single input. Each neuron in the hidden layer receives an input from each of the input neurons. Each connection is weighted, i.e., the output of neuron i that is connected to hidden neuron j is multiplied by a weight value $W_{ij}$. Similarly, the interconnection between a hidden neuron j and output neuron o is also weighted by $W_{jo}$. In the preferred embodiment, there are three output neurons: 1) normal, 2) stressed, 3) ominous. Once the specific outcome classifier 62 has been selected by the rule-based front end 58 and the appropriate variable set extracted from the feature vector, the variable set is applied to the input layer of the classifier 62. Using weights derived during training, the values at the output neurons are then predicted. To determine the classification, the output neuron with the largest predicted value is selected. If this value is greater than a threshold, currently selected to be 0.6, then this outcome is selected. If the greatest magnitude is less than this threshold, then the outcome is classified as indeterminate. For example, if the output neurons had the values normal 0.8, stressed 0.1 and ominous 0.1, the outcome would be classified as normal. If the outputs were normal 0.5, stressed 0.3, ominous 0.2, the outcome prediction would be classified as indeterminate.

Training techniques other than back propagation may also be used. Similarly, other structures, such as networks with feed-back connections, may be used. It will be understood that the type of network used is not critical to the invention. The details of neural networks which can be used to carry out the invention are described in "An Introduction to Computing with Neural Nets," by R. P. Lippmann, *IEEE ASSP Magazine*, pp. 4–22, April, 1987, and "Progress in Supervised Neural Networks," by D. R. Hush and B. G. Horne, *IEEE Signal Processing Magazine*, pp. 8–39, 1993, which are incorporated herein by reference.

Each of the classifiers 62 can be either an antepartum classifier or an active labor classifier. There are three types of antepartum classifiers. The type used depends on the signals available. For antepartum monitoring, a contraction signal is usually available. However, to make the monitor function in as many environments as practical, an antepartum mode is available that analyzes HR alone. A second classifier assumes that HR and contraction signals are available, while a third assumes that HR, contraction and fetal movement signals are all available. It is unlikely that a contraction signal will not be available when a fetal movement signal is, although this possibility is included in an alternative realization of the invention. Each neural network will have as its input time and spectral domain variables related to variability, $HR_Q$, $HR_M$, and state, as well as the outputs of the first-stage classifiers 50, 52, 54, 56. Variables related to fetal movements and contractions will be used in the appropriate classifier, if available.

An important confounding variable is gestational age of the fetus. The gestational age is input by the user. If a gestational age has not yet been entered, a default value will be used. The effects of gestational age can be accounted for in one of two ways. The method used in the monitor of the invention is that gestational age is broken down into 5 different ranges: <27 weeks, 27–30 weeks, 31–34 weeks, 35–38 weeks and >39 weeks. Gestational age is used as an input to the neural networks, with each of the ranges being assigned a constant value. Alternatively, there could be a different classifier 62 for each gestational age. The division of gestational age into the five divisions noted above is based on the present best understanding of fetal development and are presented only as an example. The ages assigned to each division as well as the number of divisions can be changed in alternative realizations and may be altered by the user.

Active labor classifiers assess fetal well-being during active labor. In order to do so in as accurate a manner as possible, in one embodiment it is assumed that a contraction signal is available. A fetal movement signal is considered optional. The design of these classifiers follows classical obstetric analysis. Therefore there is a unique classifier for each of the following conditions: 1) accelerations, 2) early decelerations, 3) late decelerations, 4) variable decelerations, 5) late/variable decelerations, 6) prolonged decelerations, 7) sinusoidal pattern, and 8) no transients. Gestational age is incorporated into the network as discussed above. Sleep state is incorporated into the network in a manner similar to that for gestational age. Each network has as inputs a unique subset from the feature vector.

The output of the neural network outcome predictor 62 selected by the rule-based front end 58 to evaluate fetal well-being will be either normal, stressed, ominous or indeterminate. The value of the predicted output will be taken as an estimate of the probability that the pattern belongs to that category. For example, if the outcome classifier predicts that the pattern is ominous and the value of the associated output neuron is 0.8, then the probability that the pattern belongs to the ominous category is 0.8.

The purpose of the rule-based back end module 64 is to organize information from previous classifiers and user input and to format the information for display to the user as well as for storage to a disk file. Information from both the expert subsystem 16 and the feature extraction subsystem 14 is selected for display by the rule-based front end module 58 and is formatted by the rule-based back end module 64. The display includes information concerning the predicted outcome, as well as variables describing the heart rate, heart rate variability, state, contraction pattern, etc.

The display and storage module 18 organizes data for display and storage in a data file. There are a number of predefined display configurations which are context sensitive, i.e., the configuration of the data on the display depends on the output of the expert subsystem 16 and the data selected by the rule-based front end module 58. In addition, the user has the ability to define a custom display configuration.

The goal of the monitor is to present sufficient information to the user in as simple a format as possible to facilitate assessment of fetal status. No clinician is likely to accept the classification made by the expert subsystem 16 without review of the data. The data used by a clinician includes data from the response to a contraction as well as the trend variables over time. To be clinically useful, such data are presented on the display in a clear and concise manner. The literature has described what the important variables are for the evaluation of a specific pattern, e.g., variable decelerations. The important variables change from one pattern to another, e.g., later decelerations versus accelerations. The invention automatically presents trend plots of the appropriate data based on the output of the classifiers. However, this can be changed by user input.

Figure 13:
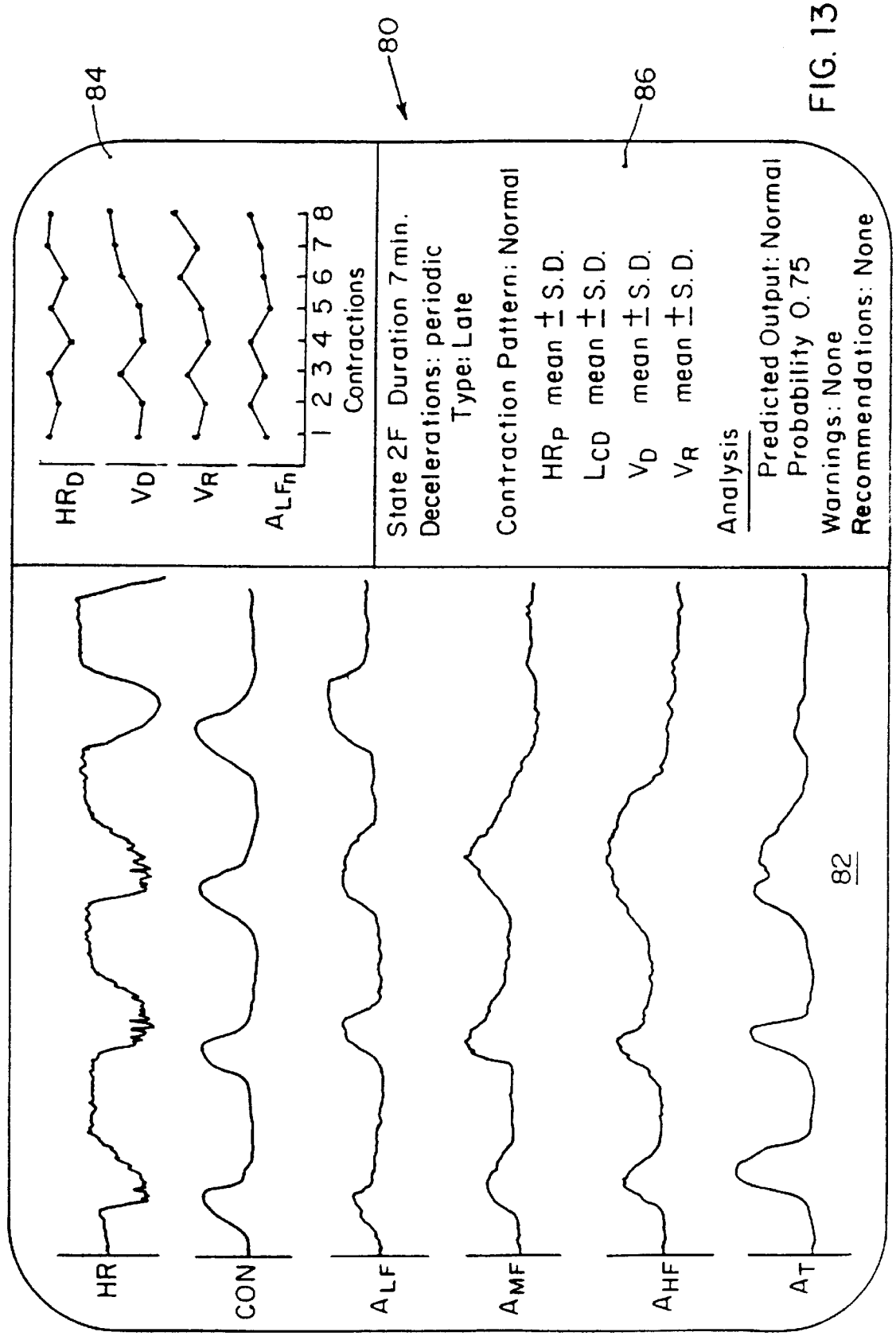
FIG. 13 is a schematic illustration of one configuration of the display of the invention.

FIG. 13 is a schematic illustration of a sample display screen 80 on the monitor 10. The display is divided into three windows. The large window 82 acts as a type of strip chart in that it displays important data as a function of time. In the default configuration for active labor, the following signals would be displayed from top to bottom: the HR time series, the contraction signal, $A_{LF}$, $A_{MF}$, $A_{HF}$, and $A_T$. This provides the clinician with a real-time display of HR, uterine activity and components of HRV. For example, this allows the clinician to view the changes in HRV during a deceleration, important information to the accurate assessment of fetal well-being. In default mode, the display graphs the last 20 minutes of data. The user can change this value to view other segments of data.

The system 10 stores templates for this window. A template is a particular configuration, of which the illustrated default is one. There are other predefined templates available which might display other combinations of variables in this window. For example, a different default template could automatically be invoked if a fetal movement signal becomes available. In this case there would be an additional trace of the occurrence of fetal movements. In addition, the user could define and store his/her own template.

The second window 84 is referred to as a "smart" window. The information displayed in this window is determined by the output of the classifiers in the expert subsystem 16. For example, where the deceleration classifier 52 determined that the decelerations were variable, the display controller would display, using a default template, trends of variables that would aid the clinician in assessing the severity of the decelerations. Thus, the window 84 displays as trends the following data from the last 8 contractions: the minimum heart rate during a deceleration, the velocity of the deceleration, the velocity of recovery, and $A_{LF}$. The user can choose to examine other variables in this window 84 such as the magnitude of the deceleration and the lag from peak contraction to the nadir of the deceleration, can choose from other default templates or can create a template of his/her own.

The third window 86 is a text window which conveys information from the output of the classifiers, some summary data, the prediction of fetal well-being, and recommendations/warnings. In the example shown, information is displayed concerning the state, contraction pattern, and deceleration pattern.

In the particular example shown in FIG. 13, the outputs of the initial four classifiers are presented, i.e., state 2 F with duration 7 minutes, periodic decelerations of type late and a normal contraction pattern. Some statistical data concerning HRV is also presented. An analysis section consists of the output of the outcome classifier with the associated probability, i.e., normal and p=0.75 for this example. The text window 86 has two additional components labeled warnings and recommendations in the figure. For this example, there are no recommendations or warnings.

For stressed or ominous classification, there will be warnings and recommendations. These will follow standard obstetric practice. For example, if a classification of ominous was made due to prolonged reduced variability, the following or a similar warning would be displayed: "prolonged reduced variability, user input indicates no narcotics have been used." This warning reminds the user that narcotics can substantially reduce HRV without causing fetal compromise. If narcotics have been administered, the user can now enter this information via the keyboard, and a new classification can be performed by the system. For this example, the following or a similar recommendation would then be displayed: "prolonged low HRV consistent with depressed fetus, if cause unknown check oxygenation status with scalp blood sample."

In an alternative embodiment, the invention provides output data to the clinician in the form of a paper strip chart with multiple data traces. In this embodiment, the variables which are displayed on the first window 82 in the previous embodiment are printed in real time on a paper strip chart. This provides the clinician with a hard copy record of past readings. As with the screen display, the user can select which variables are printed, or can rely on default templates.

Figure 14:
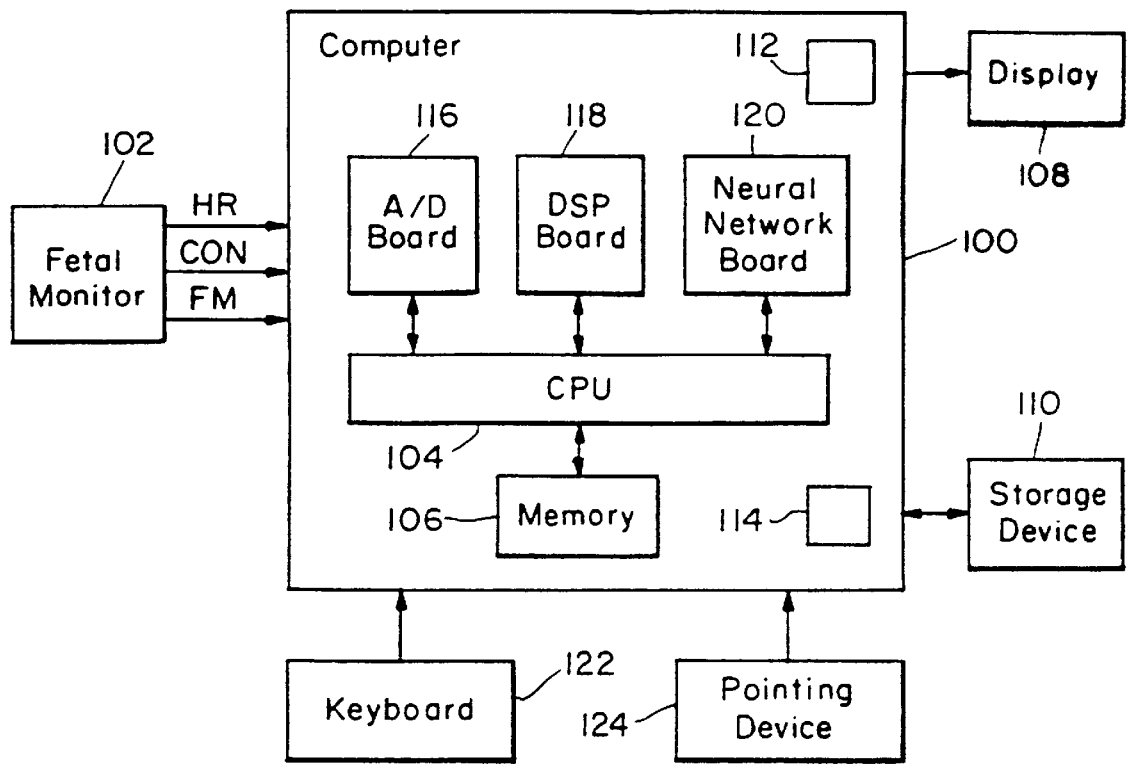
FIG. 14 is a schematic block diagram of one realization of the system of the invention.

As mentioned above, the monitoring system of the invention can be implemented in one of many different configurations. A schematic block diagram of one preferred realization is shown in FIG. 14. This realization of the invention is implemented on a personal computer (PC) 100, although other platforms such as the Macintosh, PowerPC, or a Unix system such as the SUN SPARC machines are also possible. The required input to the system is the HR time series generated by an external fetal monitor 102. Optional inputs include the contraction signal (CON) and the fetal movement (FM) signal. Typically, all signals come from a single external fetal monitor 102, although multiple monitors could be used.

The computer 100 includes a central processing unit (CPU) 104, memory 106, a display monitor 108, storage devices 110, controllers 112, 114 to drive the display and storage devices, an analog-to-digital converter (ADC) 116, a digital signal processing board (DSP) 118, and a neural network board 120. The ADC 116, DSP 118, and neural network board 120 are commercially available products. There is also an optional output board (not shown) for connection to a computer network and/or central monitoring station. Additional standard equipment can include a keyboard 122 and a mouse 124 or other suitable pointing device for providing user inputs of both data and control commands needed to execute the software which implements the various functions of the invention.

The ADC board 116 converts the analog signal from the output of the fetal monitor 102 to digital words that can be manipulated by the computer 100. In an alternative implementation, the output of the fetal monitor 102 could be connected to the computer 100 via digital outputs, e.g., a serial RS232 port. The particular implementation is determined by the output features of the particular fetal monitor.

The CPU 104 executes the software which makes the computations, controls the ADC 116, DSP 118 and neural network boards 120, and controls output to the display 108 and storage device 110 and network communication.

The purpose of the DSP board 118 is to calculate the non-linear time-frequency representation (TFR) transformation, thereby removing this computational burden from the main CPU 104. Thus, the input to the DSP board 118 is the high-pass filtered, analytic HR time series. The DSP board 118 returns to the CPU 104 the latest estimate of the TFR. The purpose of the neural network board 120 is to implement the neural network outcome predictors 62. The need for separate DSP 118 and neural network boards 120 is determined by the computational power of the main CPU 104. With recent increases in microprocessor speeds, it may not be necessary to have separate boards, since some or all of these functions could be handled by the CPU 104. The need for the separate boards is also determined by the precise platform on which the invention is implemented, e.g., SUN workstations being faster than PCs.

In an alternative realization which is also computer based, a HR time series of sufficient accuracy may not be available from the fetal monitor. In this case, the fetal ECG signal is acquired by the computer via either the ADC board 116 or over digital communication lines. In this realization, another software module is required to perform R-wave recognition and construction of the HR time series. These latter functions can also be implemented on a DSP board, possibly separate from the DSP board which calculates the TFR, within the computer.

Figure 15:
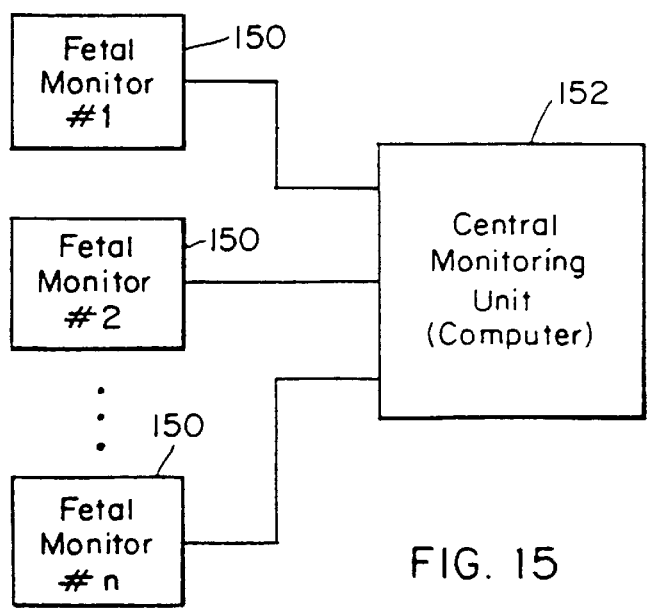
FIG. 15 is a schematic block diagram of an alternative realization of the system of the invention.

A schematic block diagram of another realization of the invention is shown in FIG. 15. In this realization, the calculation of the time-frequency representation is incorporated into a stand-alone fetal monitor 150, while the classification and prediction tasks are implemented on a digital computer or central monitoring unit 1S2. This configuration relieves the digital computer 152 of substantial computation load. Consequently, the computer 152 can also function as a central monitoring station, in which it performs classifications and predictions of multiple patients, each monitored by a fetal monitor 150. By calculating the TFR within the fetal monitor 150, signals related to HRV, i.e., the areas under the TFR, can be output to a strip chart in addition to the usual HR and contraction signals. This provides the clinician with much needed quantitative information concerning HRV. Also, since the classifications and predictions are generated at the remote central monitoring unit 152, they are not displayed where the patient can view them and become upset, possibly needlessly.

Figure 16:
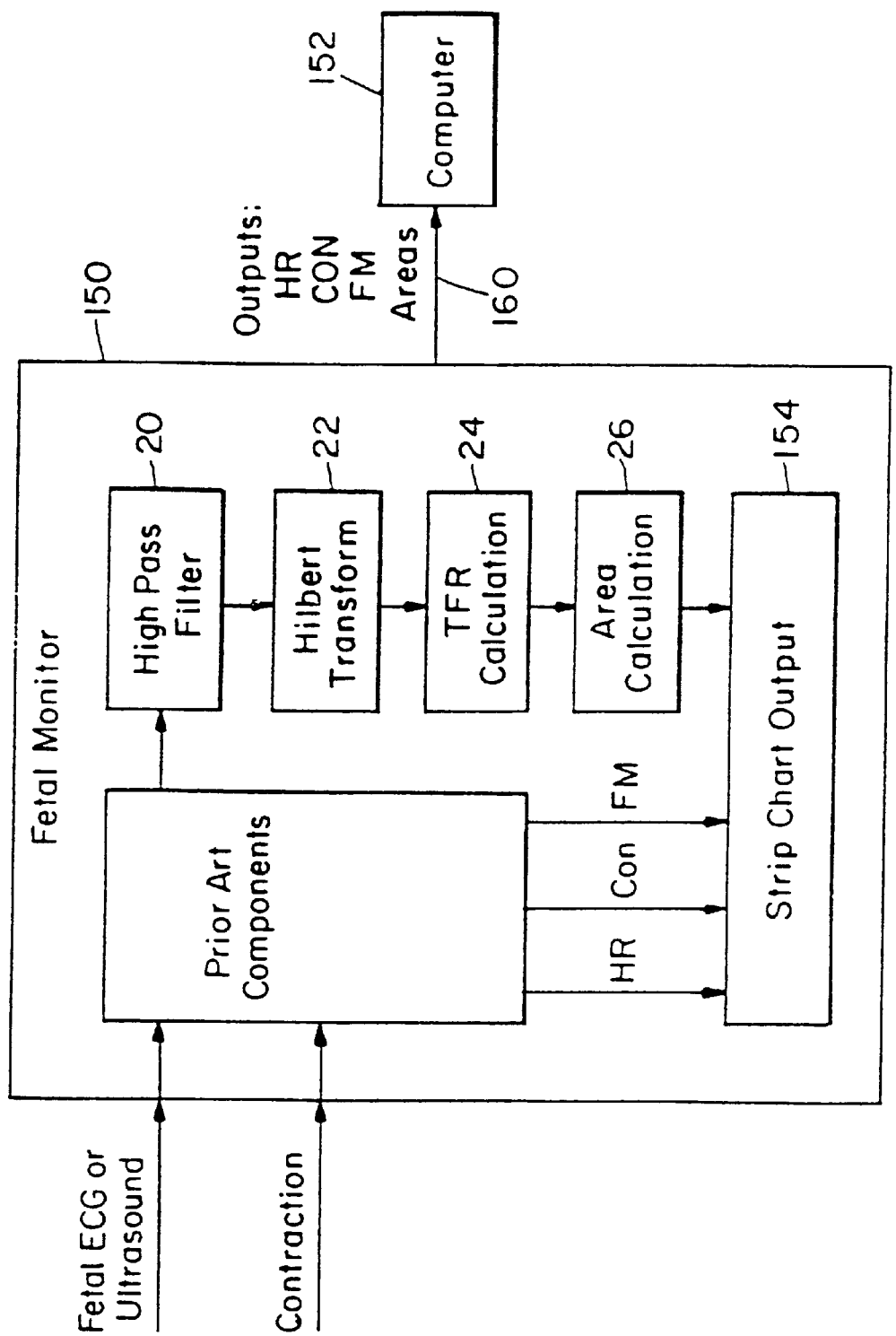
FIG. 16 is a schematic block diagram of the fetal monitor used in the realization of the invention shown in FIG. 15.

One embodiment of this realization implements the calculation of the TFR in hardware. This hardware is incorporated into a fetal monitor where the heart rate signal is available from commercially available components. A schematic block diagram of this portion of the realization is shown in FIG. 16. The inputs are the usual signals for determining HR (fetal ECG and ultrasound) and the contraction signal. The block labeled Prior Art Components 156 contains the processors which extract the HR time series from the input signals. This HR time series signal is then output to the components of the invention beginning with the high-pass filter 20. The filtered HR times series is then forwarded to the Hilbert Transformer 22 which makes the signal analytic. The analytic filtered signal is then passed to the processor 24 which calculates the TFR. The amplitude spectrum from the TFR calculation is passed to the next processor 26 which calculates the areas under the curve over predefined frequency bands. The output of the area calculation processor 26 is then available for display on the strip chart 154.

The HR signal is output to the strip chart as are the contraction and FM signals if they are available. One or more of the areas (or sum and/or ratios of the various areas) are also output to the strip chart 154. There is a default setting which includes total area $A_T$. Other signal (s) could be selected by user input. By displaying $A_T$, along with HR and contraction signals, the system enables the clinician to better evaluate HRV and, thus, fetal well-being. All variables, including HR, CON, FM, and the areas, are available for output to the central monitoring station 152 via digital communication lines 160.

The central monitoring station 152 is a computer-based system which performs the functions of the feature extraction subsystem 14, expert subsystem 16, and display and storage module 18 shown in FIG. 8. Additional software modules are included to allow monitoring of a number of remote fetal monitors 150 as well as classification of more than one fetus.

Figure 17:
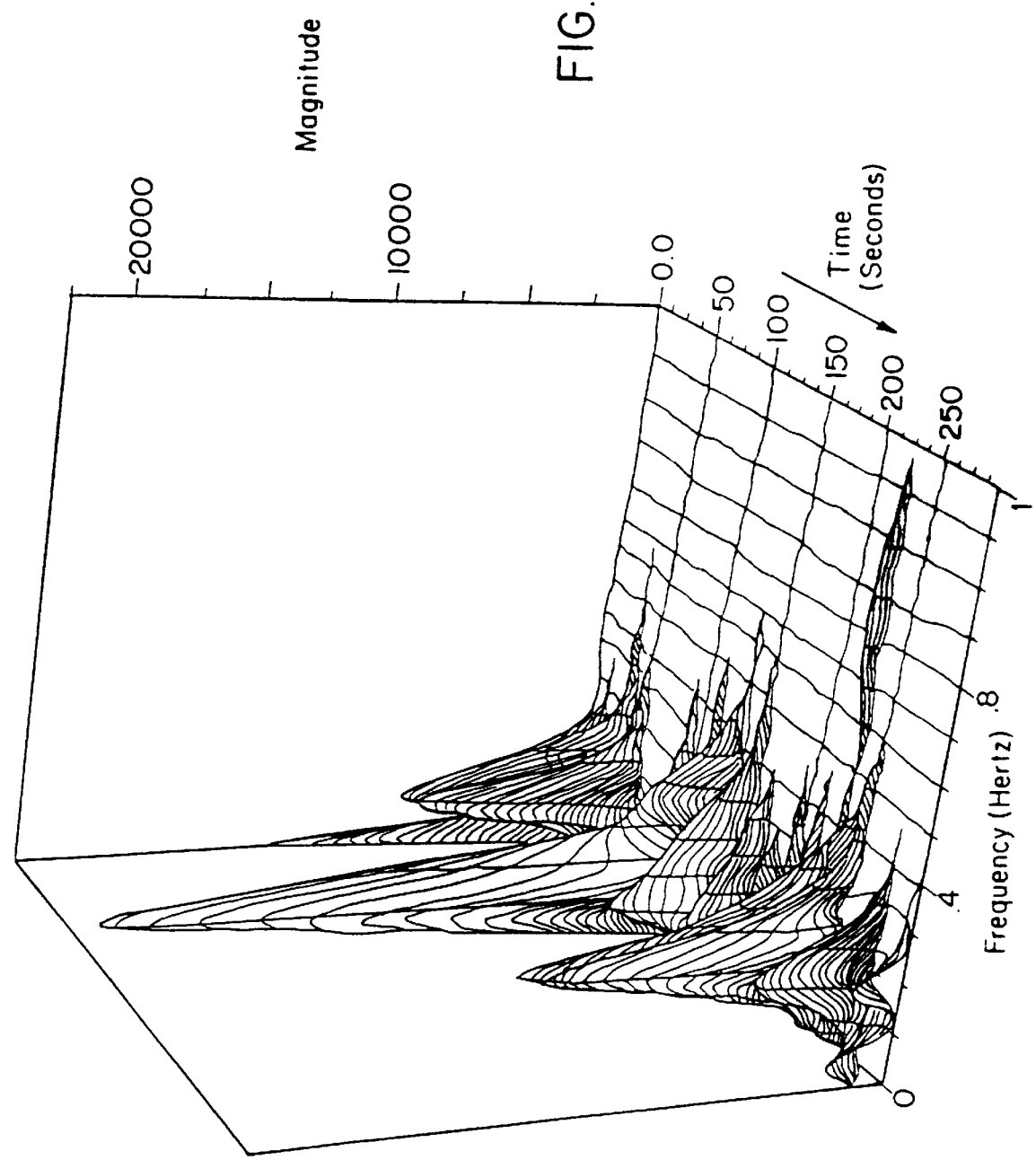
FIG. 17 is a schematic illustration of a three-dimensional plot of the time-frequency representation of the invention which can be produced on the display of the invention.

In one preferred embodiment of the invention, the user has the option of reviewing the raw TFR data at any time or can substitute a three-dimensional display of the TFR for one of the three display windows described above. The user can also optionally fill the entire display with the three-dimensional TFR display. An example of the three-dimensional TFR plot is shown in FIG. 17. The example of FIG. 17 shows a smoothed Wigner spectrum in the form of frequency-versus-magnitude calculated on fetal heart rate over time. The plot represents the spectral content of the heart rate signal over a frequency range of 0 to 1 Hz for five minutes of data where the spectra were calculated at 1.0-second intervals. Such a plot is rich in detail regarding fetal heart rate variability. First, an overall indication of HRV is obtained. A moribund fetus would have a relatively flat spectrum over the observation time. In addition, a plot over a longer period, e.g., 20 minutes, would enable the clinician to clearly observe a change in sleep state, since such changes are associated with well documented changes in HRV. This is particularly important in cases where HRV is low where it is critical to determine whether the fetus is sleeping or in distress.

A plot such as the one in FIG. 17 also provides the clinician with a great deal of information concerning transient changes in fetal HRV. Such transient changes are important in interpreting decelerations during labor. Increases in variability during a deceleration indicate the presence of intact compensatory mechanisms in the fetus and can therefore be reassuring. However, decreased variability during a deceleration is considered an ominous sign. Transient changes observed over a certain range of frequencies will also aid in fetal assessment. As an example, the transient increase in the Wigner distribution shown in FIG. 17 in the frequency range 0.5 to 1.0 Hz at approximately 225 seconds is consistent with respiratory modulated changes in HRV. Such indices of fetal breathing are important in fetal assessment. Finally, the appearance of a sinusoidal pattern, which has important diagnostic implications, would be easily identified from such a plot as well defined sharp peak in the spectra.

The three-dimensional TFR plot of FIG. 17 can also be displayed alongside a plot of other timing signals such as the uterine contraction signal or the fetal movement signal. The clinician can use the visual display to quickly ascertain the relationships among the various signals. For example, the clinician can readily identify late and/or early decelerations in HRV with respect to uterine contractions as part of the process of determining overall fetal well-being. Alternatively, the TFR plot can be color coded to indicate uterine contractions such as by plotting the TFR in one color during a contraction and in another color between contractions.

While this invention has been particularly shown and described with references to preferred embodiments thereof, it will be understood by those skilled in the art that various changes in form and details may be made therein without departing from the spirit and scope of the invention as defined by the appended claims.

We claim:

1. A fetal data processing method comprising:
   receiving a signal indicative of fetal heart rate time data for the fetus;
   generating a time-frequency representation based on the fetal heart rate time data; and
   analysing the time-frequency representation using the fetal heart rate time data to indicate a condition of the fetus.

2. The method of claim 1 further comprising analyzing transient change in fetal heart rate variability.

3. The method of claim 1 further comprising indicating transient change in fetal heart rate.

4. The method of claim 1 wherein the analyzing step further comprises using a feature extraction system to form a feature vector.

5. The method of claim 1 wherein a uterine contraction signal is used to perform the analyzing step.

6. The method of claim 1 wherein a fetal movement signal is used to perform the analyzing step.

7. The method of claim 1 further comprising predicting outcome for the fetus.

8. The method of claim 1 wherein the analyzing step comprises applying a set of classification rules to fetal data.

9. The method of claim 1 wherein the analyzing step comprises applying a pattern of fetal data to a neural network.

10. The method of claim 1 wherein the analyzing step comprises analyzing the time-frequency representation in plural frequency bands.

11. The method of claim 1 wherein the time-frequency representation spans a frequency range from 0.02 Hz to 1.1 Hz.

12. The method of claim 1 wherein the analyzing step comprises computing areas of the time-frequency representation.

13. The method of claim 1 wherein the time-frequency representation is generated for fetal heart rate time data from a time period of less than ten seconds.

14. The method of claim 1 further comprising sampling the fetal heart rate time data at a frequency greater than 2 Hz.

15. The method of claim 1 further comprising displaying in real time variables used to indicate the condition of the fetus.

16. The method of claim 1 further comprising displaying a three-dimensional image of the time-frequency representation.

17. The method of claim 1 further comprising generating recommendations regarding fetal well-being.

18. The method of claim 1 wherein the time-frequency representation is a non-linear time-frequency representation.

19. The method of claim 1 wherein the time-frequency representation is generated using a smoothed Wigner distribution.

20. A fetal data processing system comprising:
    an input that receives fetal heart rate time data for a fetus; and
    a processing system comprising:
       a transformation subsystem that receives the fetal heart rate time data and generates a time-frequency representation for the fetal heart rate time data, and
       a variable analysis subsystem that receives the time-frequency representation and fetal condition data and generates a variable representation of fetal condition.

21. The fetal data processing system of claim 20 further comprising a classifying subsystem that analyzes the fetal heart rate time data to indicate a condition of the fetus.

22. The fetal data processing system of claim 21 wherein the classifying subsystem analyzes a uterine contraction signal to indicate the condition of the fetus.

23. The fetal data processing system of claim 21 wherein the classifying subsystem analyzes a fetal movement signal to indicate the condition of the fetus.

24. The fetal data processing system of claim 21 wherein the classifying subsystem analyzes the time-frequency representation in plural frequency bands.

25. The fetal data processing system of claim 21 wherein the classifying subsystem applies a set of classifying rules to a pattern of fetal data to classify the fetal data.

26. The fetal data processing system of claim 21 wherein the classifying subsystem comprises at least one neural network for receiving a pattern of fetal data to classify the fetal data.

27. The fetal data processing system of claim 21 wherein the classifying subsystem comprises a plurality of neural networks that receive patterns of fetal data to classify the fetal data.

28. The fetal data processing system of claim 21 wherein the classifying subsystem predicts an outcome for the fetus.

29. The fetal data processing system of claim 20 further comprising a display for displaying in real time variables used to indicate the condition of the fetus.

30. The fetal data processing system of claim 20 further comprising a display controller for selecting for display in real time variables used to predict outcome for the fetus.

31. The fetal data processing system of claim 20 further comprising a display displaying recommendations regarding fetal well-being.

32. The fetal data processing system of claim 20 further comprising a fetal monitor providing the fetal heart rate time data.

33. The fetal data processing system of claim 20 wherein the transformation subsystem generates the time-frequency representation based on fetal heart rate time data from a time period not greater than 10 seconds.

34. The fetal data processing system of claim 20 further comprising a display for displaying a three-dimensional plot of the time-frequency representation.

35. The fetal data processing system of claim 20 wherein the time-frequency representation generated by the processing system is a non-linear time-frequency representation.

36. A fetal data processing system comprising:
    an input that receives fetal heart rate time data for a fetus; and
    a processing system comprising:
       a transformation subsystem that receives the fetal heart rate time data and generates a time-frequency representation for the fetal heart rate time data; and
       a variable analysis subsystem that receives the time-frequency representation and fetal condition data and generates a variable representation of fetal condition; and
    a display that displays a three-dimensional plot of the time-frequency representation.

* * * * *